(12) United States Patent
Nakano et al.

(10) Patent No.: US 10,103,338 B1
(45) Date of Patent: *Oct. 16, 2018

(54) ORGANIC ELECTROLUMINESCENCE DEVICE AND ELECTRONIC DEVICE

(71) Applicant: IDEMITSU KOSAN CO., LTD., Tokyo (JP)

(72) Inventors: Yuki Nakano, Sodegaura (JP); Hirokatsu Ito, Sodegaura (JP); Tetsuya Masuda, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/823,558

(22) Filed: Nov. 27, 2017

Related U.S. Application Data

(63) Continuation of application No. 15/817,149, filed on Nov. 17, 2017.

(30) Foreign Application Priority Data

Aug. 14, 2017 (JP) .................................. 2017-156472

(51) Int. Cl.
*H01L 51/50* (2006.01)
*H01L 51/00* (2006.01)
(Continued)

(52) U.S. Cl.
CPC ........ *H01L 51/0073* (2013.01); *C07D 209/86* (2013.01); *C07D 307/91* (2013.01);
(Continued)

(58) Field of Classification Search
None
See application file for complete search history.

(56) References Cited

U.S. PATENT DOCUMENTS

2008/0014464 A1 1/2008 Kawamura et al.
2008/0315754 A1 12/2008 Kawamura et al.
(Continued)

FOREIGN PATENT DOCUMENTS

JP 2005-314239 A 11/2005
JP 2006-151844 6/2006
(Continued)

OTHER PUBLICATIONS

U.S. Office Action on U.S. Appl. No. 15/817,149 dated Jan. 18, 2018.
(Continued)

*Primary Examiner* — Gregory D Clark
(74) *Attorney, Agent, or Firm* — Foley & Lardner

(57) ABSTRACT

An organic electroluminescence device comprising an anode, a cathode and an organic layer between the anode and the cathode, the organic layer comprising an emitting layer and at least one layer between the emitting layer and the
(Continued)

anode, the emitting layer comprising a compound represented by the following formula (1), and the at least one layer between the emitting layer and the anode comprising a compound represented by the following formula (2):

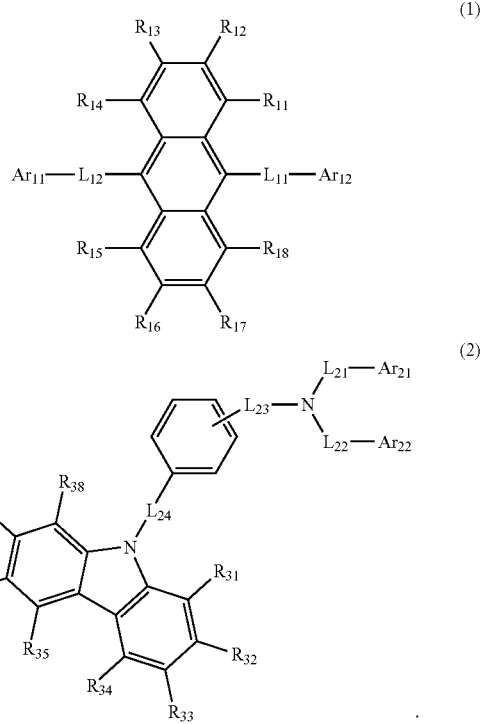

26 Claims, 1 Drawing Sheet

(51) Int. Cl.
    *C07D 307/91* (2006.01)
    *C07D 209/86* (2006.01)
    *C09K 11/06* (2006.01)

(52) U.S. Cl.
    CPC .......... *C09K 11/06* (2013.01); *H01L 51/0072* (2013.01); *H01L 51/5012* (2013.01); *H01L 51/5056* (2013.01); *C09K 2211/1029* (2013.01); *C09K 2211/1088* (2013.01)

(56) References Cited

U.S. PATENT DOCUMENTS

| | | |
|---|---|---|
| 2010/0045170 A1 | 2/2010 | Lee et al. |
| 2010/0245217 A1 | 9/2010 | Nomura et al. |
| 2010/0295029 A1 | 11/2010 | Kawamura |
| 2011/0068683 A1 | 3/2011 | Kawamura et al. |
| 2012/0112169 A1 | 5/2012 | Mizuki et al. |
| 2013/0153878 A1 | 6/2013 | Mizuki et al. |
| 2013/0313538 A1 | 11/2013 | Kawamura et al. |
| 2014/0103319 A1 | 4/2014 | Kawamura et al. |
| 2014/0151670 A1 | 6/2014 | Lee et al. |
| 2015/0325800 A1 | 11/2015 | Ito et al. |
| 2016/0005976 A1 | 1/2016 | Mizuki et al. |
| 2016/0020403 A1 | 1/2016 | Kawamura et al. |
| 2016/0079542 A1 | 3/2016 | Itoi |
| 2016/0181542 A1 | 6/2016 | Kawamura et al. |
| 2016/0329500 A1 | 11/2016 | Lee et al. |
| 2016/0380198 A1 | 12/2016 | Mizuki et al. |
| 2017/0222153 A1 | 8/2017 | Kawamura et al. |

FOREIGN PATENT DOCUMENTS

| | | | | |
|---|---|---|---|---|
| JP | 2009-076817 | * | 4/2009 | ............ H01L 51/50 |
| JP | 2010-222261 A | | 10/2010 | |
| JP | 2016-058549 A | | 4/2016 | |
| KR | 100910150 B1 | | 7/2009 | |
| KR | 1020120135501 A | | 12/2012 | |
| WO | WO-2007/148660 A1 | | 12/2007 | |
| WO | WO-2008/143229 A1 | | 11/2008 | |
| WO | WO-2009/063846 A1 | | 5/2009 | |
| WO | WO-2009/069537 A1 | | 6/2009 | |
| WO | WO-2009/116628 A1 | | 9/2009 | |
| WO | WO-2009/154207 A1 | | 12/2009 | |
| WO | WO-2010/010924 A1 | | 1/2010 | |
| WO | WO-2010/052885 A1 | | 5/2010 | |
| WO | WO-2010/122810 A1 | | 10/2010 | |
| WO | WO-2014/014307 A1 | | 1/2014 | |
| WO | WO-2014/073306 A1 | | 5/2014 | |
| WO | WO-2016/013735 A1 | | 1/2016 | |
| WO | WO 2016/027938 | * | 2/2016 | ............ H01L 50/50 |

OTHER PUBLICATIONS

U.S. Office Action on U.S. Appl. No. 15/823,556 dated Jan. 18, 2018.

* cited by examiner

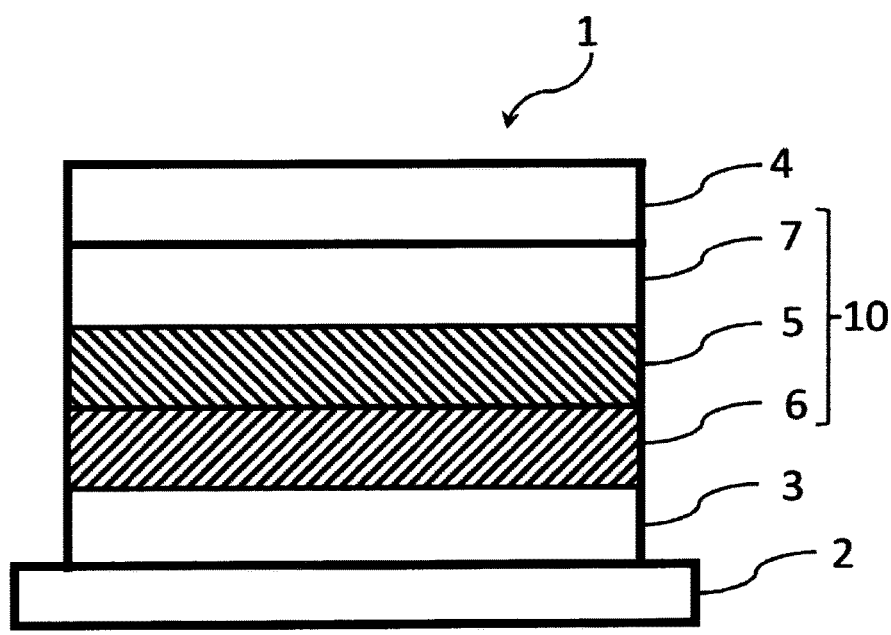

ORGANIC ELECTROLUMINESCENCE DEVICE AND ELECTRONIC DEVICE

CROSS-REFERENCED TO RELATED PATENT APPLICATIONS

The present application is a Continuation of U.S. patent application Ser. No. 15/817,149, filed Nov. 17, 2017, which claims priority from Japanese Application No. 2017-156472, filed Aug. 14, 2017 the contents of which are hereby incorporated by reference in their entirety.

TECHNICAL FIELD

The invention relates to an organic electroluminescence device and an electronic device.

BACKGROUND ART

When a voltage is applied to an organic electroluminescence device (hereinafter often referred to as an "organic EL device"), holes and electrons are injected to an emitting layer from an anode and a cathode, respectively, and injected holes and electrons are re-combined to form excitons.

An organic EL device comprises an emitting layer between an anode and a cathode. Further, it may have a stacked layer structure comprising an organic layer such as a hole-injecting layer, a hole-transporting layer, an electron-injecting layer, an electron-transporting layer, etc.

Patent Documents 1 to 12 disclose an anthracene derivative to which dibenzofuran bonds, used in an organic EL device.

Patent Document 13 discloses a monoamine derivative to which carbazole bonds, used in an organic EL device.

Patent Document 14 discloses combined use of an anthracene derivative to which dibenzofuran bonds and a monoamine derivative.

Patent Document 15 discloses an organic EL device in which a layer that is adjacent to an emitting layer comprises a monoamine derivative to which a N-carbazolyl group bonds and the emitting layer comprises an anthracene derivative.

RELATED ART DOCUMENTS

Patent Documents

Patent Document 1: WO2010/122810
Patent Document 2: WO2008/143229
Patent Document 3: JP-A-2005-314239
Patent Document 4: WO2014/014307
Patent Document 5: WO2009/069537
Patent Document 6: WO2009/063846
Patent Document 7: WO2009/116628
Patent Document 8: WO2010/052885
Patent Document 9: WO2009/154207
Patent Document 10: WO2010/010924
Patent Document 11: Korean Patent Publication No. 2012-0135501
Patent Document 12: Korean Patent No. 10-0910150
Patent Document 13: WO2007/148660
Patent Document 14: WO2016/013735
Patent Document 15: JP-A-2016-58549

SUMMARY OF THE INVENTION

Problems to be Solved by the Invention

An object of the invention is to provide an organic EL device having improved luminous efficiency.

Means for Solving the Problems

According to one aspect of the invention, the following organic electroluminescence device is provided.

An organic electroluminescence device comprising an anode, a cathode and an organic layer between the anode and the cathode,
the organic layer comprising an emitting layer and at least one layer between the emitting layer and the anode,
the emitting layer comprising a compound represented by the following formula (1), and
the at least one layer between the emitting layer and the anode comprising a compound represented by the following formula (2):

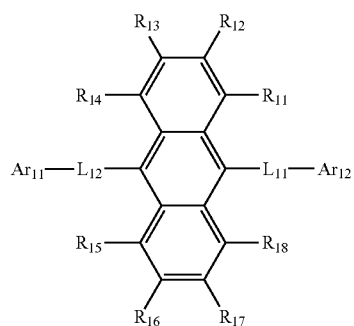

(1)

wherein in the formula (1),
$R_{11}$ to $R_{18}$ are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group having 2 to 50 carbon atoms, a substituted or unsubstituted cycloalkyl group including 3 to 50 carbon atoms that form a ring (hereinafter referred to as "ring carbon atoms"), a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{101}$)($R_{102}$)($R_{103}$), —C(=O)$R_{104}$, —COOR$_{105}$, —N($R_{106}$)($R_{107}$), a halogen atom, a cyano group, a nitro group, a substituted or unsubstituted aryl group including 6 to 50 ring carbon atoms, or a substituted or unsubstituted heterocyclic group including 5 to 50 atoms that form a ring (hereinafter referred to as "ring atoms"),
$R_{101}$ to $R_{107}$ are independently a hydrogen atom, a substituted or unsubstituted alkyl group including 1 to 50 carbon atoms, a substituted or unsubstituted aryl group including 6 to 50 ring carbon atoms or a substituted or unsubstituted heterocyclic group including 5 to 50 ring atoms,
when two or more $R_{101}$ to $R_{107}$ are present, the two or more of each of $R_{101}$ to $R_{107}$ may be the same or different, at least one of $Ar_{11}$ and $Ar_{12}$ is a monovalent group represented by the following formula (11):

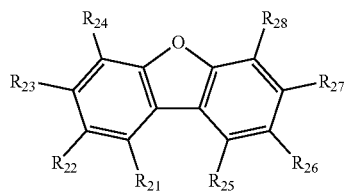

wherein the formula (11), one of $R_{21}$ to $R_{28}$ is a single bond bonding to $L_{11}$ or $L_{12}$, $R_{21}$ to $R_{28}$ that do not bond to $L_{11}$ or $L_{12}$ are independently a hydrogen atom, an alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, $-Si(R_{101})(R_{102})(R_{103})$, $-C(=O)R_{104}$, $-COOR_{105}$, $-N(R_{106})(R_{107})$, a halogen atom, a cyano group, a nitro group, a substituted or unsubstituted aryl group including 6 to 50 ring carbon atoms or a substituted or unsubstituted heterocyclic group including 5 to 50 ring atoms, $R_{101}$ to $R_{107}$ are as defined as above, $Ar_{11}$ or $Ar_{12}$ that is not a monovalent group represented by the formula (11) is a substituted or unsubstituted aryl group including 6 to 50 ring carbon atoms, $L_{11}$ and $L_{12}$ are independently a single bond, a substituted or unsubstituted alkylene group including 1 to 50 carbon atoms, a substituted or unsubstituted arylene group including 6 to 50 ring carbon atoms or a substituted or unsubstituted divalent heterocyclic group including 5 to 50 ring atoms,

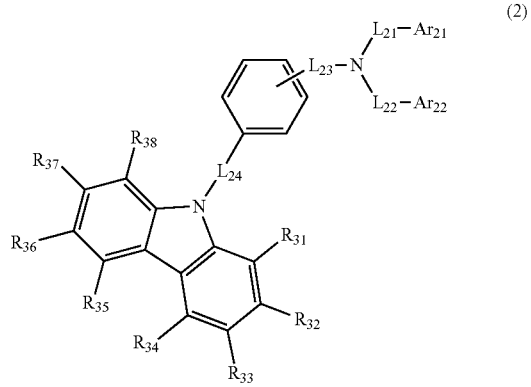

wherein in the formula (2), one or more pairs of two or more adjacent groups of $R_{31}$ to $R_{38}$ may form a substituted or unsubstituted saturated or unsaturated ring, and $R_{31}$ to $R_{38}$ that do not involve the ring formation are independently a hydrogen atom, an alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, an alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, $-Si(R_{201})(R_{202})(R_{203})$, $-C(=O)R_{204}$, $-COOR_{205}$, a halogen atom, a cyano group, a nitro group, a substituted or unsubstituted aryl group including 6 to 50 ring carbon atoms or a substituted or unsubstituted heterocyclic group including 5 to 50 ring atoms, $R_{201}$ to $R_{205}$ are independently a hydrogen atom, a substituted or unsubstituted alkyl group including 1 to 50 carbon atoms, a substituted or unsubstituted aryl group including 6 to 50 ring carbon atoms or a substituted or unsubstituted heterocyclic group including 5 to 50 ring atoms, when two or more $R_{201}$ to $R_{205}$ are present, the two or more of each of $R_{201}$ to $R_{205}$ may be the same or different, $L_{21}$ to $L_{24}$ are independently a single bond, a substituted or unsubstituted alkylene group including 1 to 50 carbon atoms, a substituted or unsubstituted arylene group including 6 to 50 ring carbon atoms or a substituted or unsubstituted divalent heterocyclic group including 5 to 50 ring atoms; and $Ar_{21}$ and $Ar_{22}$ are independently a substituted or unsubstituted aryl group including 6 to 50 ring carbon atoms or a substituted or unsubstituted heterocyclic group including 5 to 50 ring atoms.

According to another embodiment of the invention, an electronic device provided with the above-mentioned organic electroluminescence device is provided.

Advantageous Effects of the Invention

According to the invention, it is possible to provide an organic EL device having improved luminous efficiency.

BRIEF DESCRIPTION OF THE DRAWINGS

FIG. 1 is a view showing a schematic configuration of one embodiment of the organic EL device of the invention.

MODE FOR CARRYING OUT THE INVENTION

In the present specification, a hydrogen atom includes isomers differing in number of neutrons, i.e. protium, deuterium and tritium.

In the present specification, the number of "ring carbon atoms" means the number of carbon atoms among atoms constituting a ring of a compound in which atoms are bonded in the form of a ring (for example, a monocyclic compound, a fused ring compound, a cross-linked compound, a carbocyclic compound or a heterocyclic compound). When the ring is substituted by a substituent, the carbon contained in the substituent is not included in the number of ring carbon atoms. The same is applied to the "ring carbon atoms" mentioned below, unless otherwise indicated. For example, a benzene ring includes 6 ring carbon atoms, a naphthalene ring includes 10 ring carbon atoms, a pyridinyl group includes 5 ring carbon atoms, and a furanyl group includes 4 ring carbon atoms. When a benzene ring or a naphthalene ring is substituted by an alkyl group as a substituent, for example, the number of carbon atoms of the alkyl group is not included in the number of ring carbon atoms. When a fluorene ring is bonded with a fluorene ring as a substituent (including a spirofluorene ring), for example, the number of carbon atoms of the fluorene ring as the substituent is not included in the number of ring carbon atoms.

In the present specification, the number of "ring atoms" means the number of atoms constituting a ring of a compound in which atoms are bonded in the form of a ring (for example, a monocyclic compound, a fused ring compound, a cross-linked compound, a carbocyclic compound or a heterocyclic compound). It does not include atoms which do not involve the ring formation (for example, a hydrogen atom that terminates the atomic bonding of the atom constituting a ring) and atoms which when the ring is substituted by a substituent, the atom contained in the substituent. The same is applied to the "ring atoms" mentioned below, unless otherwise indicated. For example, a pyridine ring includes 6 ring carbon atoms, a quinazoline ring includes 10 ring atoms, and a furan ring includes 5 ring atoms. Hydrogen atoms respectively bonded to a carbon atom of a pyridine ring or a quinazoline ring or atoms constituting a substituent are not included in the number of ring atoms. When a fluorene ring is bonded with a fluorene ring as a substituent (including a spirofluorene ring), for example, the number of atoms of the fluorene ring as a substituent is not included in the number of ring atoms.

In the present specification, the "XX to YY carbon atoms" in the "substituted or unsubstituted ZZ group including XX to YY carbon atoms" means the number of carbon atoms when the ZZ group is unsubstituted. The number of carbon atoms of a substituent when the group is substituted is not included. Here, "YY" is larger than "XX", and "XX" and "YY" independently an integer of 1 or more.

In the present specification, the "XX to YY atoms" in the "substituted or unsubstituted ZZ group including XX to YY atoms" means the number of atoms when the ZZ group is unsubstituted. The number of atoms of a substituent when the group is substituted is not included. Here, "YY" is larger than "XX", and "XX" and "YY" independently an integer of 1 or more.

In the present specification, the "unsubstituted" in the "substituted or unsubstituted" means bonding of a hydrogen atom, not substitution by the substituent mentioned above.

As specific examples of each group in the present specification, the following can be given.

As examples of an unsubstituted alkyl group including 1 to 50 (preferably 1 to 30, more preferably 1 to 18, and further preferably 1 to 5) carbon atoms, a methyl group, an ethyl group, a propyl group, an isopropyl group, an n-butyl group, a s-butyl group, an isobutyl group, a t-butyl group, an n-pentyl group, an n-hexyl group, an n-heptyl group, an n-octyl group or the like can be given.

As examples of the substituted alkyl group including 1 to 50 (preferably 1 to 30, more preferably 1 to 18, and further preferably 1 to 5) carbon atoms, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodeethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a 1-pyrrolylmethyl group, a 2-(1-pyrrolyl)ethyl group, a 1-hydroxy-2-phenylisopropyl, 1-chloro-2-phenyl-isopropyl group or the like can be given.

As the unsubstituted alkenyl group including 2 to 50 (preferably 2 to 30, more preferably 2 to 18) carbon atoms, a vinyl group, an allyl group, a 1-butenyl group, a 2-butenyl group, a 3-butenyl group, a 1,3-butanedienyl group, a 1-methylvinyl group, a 1-methylallyl group, a 1,1-dimethylallyl group, a 2-methylallyl group, a 1,2-dimethylallyl group or the like can be given.

As the unsubstituted alkynyl group including 2 to 50 (preferably 2 to 30, more preferably 2 to 18) carbon atoms, an ethynyl group or the like can be given.

As the unsubstituted cycloalkyl group including 3 to 50 (preferably 3 to 30, more preferably 3 to 18, and further preferably 3 to 6) ring carbon atoms, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group or the like can be given.

The unsubstituted alkoxy group including 1 to 50 (preferably 1 to 30, more preferably 1 to 18) carbon atoms is represented by —OX, and as examples of X, the above-mentioned alkyl group including 1 to 50 carbon atoms can be given, for example.

The unsubstituted alkylthio group including 1 to 50 (preferably 1 to 30, more preferably 1 to 18) carbon atoms is represented by —SX, and as examples of X, the above-mentioned alkyl group including 1 to 50 carbon atoms can be given, for example.

As the unsubstituted aryl group including 6 to 50 (preferably 6 to 30, more preferably 6 to 18) ring carbon atoms, a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group or the like can be given.

Among these, a phenyl group, a naphthyl group, a biphenylyl group, a terphenyl group, a pyrenyl group, a phenanthryl group and a fluorenyl group are preferable, with a phenyl group, a naphthyl group, a biphenylyl group, a terphenyl group, a pyrenyl group and a fluorenyl group being more preferable.

As the substituted aryl group including 6 to 50 (preferably 6 to 30, more preferably 6 to 18) ring carbon atoms, an o-tolyl group, a m-tolyl group, a p-tolyl group, a para-isopropylphenyl group, a meta-isopropylphenyl group, an ortho-isopropylphenyl group, a p-t-butylphenyl group, a meta-t-butylphenyl group, an ortho-t-butylphenyl group, a 3,4,5-trimethylphenyl group, a 4-phenoxyphenyl group, a 4-methoxyphenyl group, a 3,4-dimethoxyphenyl group, a 3,4,5-trimethoxyphenyl group, a 4-(phenylsulfanyl)phenyl group, a 4-(methylsulfanyl) phenyl group, a N',N'-dimethyl-N-phenyl group, a N',N'-dimethyl-N-phenyl group, a 2,6-dimethylphenyl group, a (2-phenylpropyl)phenyl group, a 3-methyl-2-naphthyl group, a 4-methyl-1-naphthyl group, a 4-methyl-1-anthryl group, a 4'-methylbiphenylyl group, a 4''-t-butyl-p-terphenyl-4-yl group, a 9,9-dimethylfluorenyl group, a 9,9-diphenylfluorenyl group, a 9,9'-spirobifluorenyl group, a 9,9-di(4-methylphenyl)fluorenyl group, a 9,9-di(4-isopropylphenyl)fluorenyl group, a 9,9-di(4-t-butylphenyl)fluorenyl group, a chrysenyl group, a fluororanthenyl group or the like can be given, for example.

As the unsubstituted arylene group including 6 to 50 (preferably 6 to 30, more preferably 6 to 18) ring carbon atoms, a divalent group formed from an aromatic hydrocarbon ring constituting the above-exemplified aryl group including 6 to 50 ring carbon atoms can be given, for example. Specifically, a divalent group formed from a phenyl group includes o-, m- and p-phenylene groups, a divalent group formed from a biphenylyl group includes 2,4'-biphenyldiyl, 3,4'-biphenyldiyl and 4,4'-biphenyldiyl groups, and a divalent group formed from a naphthyl group includes naphthalen-1,2-diyl, naphthalen-1,3-diyl, naphthalen-1,4-diyl, naphthalen-1,5-diyl, naphthalen-1,6-diyl, naphthalen-1,7-diyl, naphthalen-1,8-diyl, naphthalen-2,3-diyl, naphthalen-2,6-diyl and naphthalen-2,7-diyl groups, for example.

The unsubstituted aryloxy group including 6 to 50 (preferably 6 to 30, more preferably 6 to 18) ring carbon atoms is represented by —OY, and as examples of Y, the above-mentioned aryl group including 6 to 50 ring carbon atoms can be given, for example.

The unsubstituted arylthio group including 6 to 50 (preferably 6 to 30, more preferably 6 to 18) ring carbon atoms is represented by —SY, and as examples of Y, the above-mentioned aryl group including 6 to 50 ring carbon atoms can be given, for example.

As the unsubstituted aralkyl group including 7 to 50 (preferably 7 to 30, more preferably 7 to 18) carbon atoms, a benzyl group, a 1-phenylethyl group, a 2-phenylethyl group, a 1-phenylisopropyl group, a 2-phenylisopropyl group, a phenyl-t-butyl, a α-naphthylethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group or the like can be given, for example.

As the substituted aralkyl group including 7 to 50 (preferably 7 to 30, more preferably 7 to 18) carbon atoms, a p-methylbenzyl group, a m-methylbenzyl group, an o-methylbenzyl group, a p-chlorobenzyl group, a m-chlorobenzyl group, an o-chlorobenzyl group, a p-bromobenzyl group, a m-bromobenzyl group, an o-bromobenzyl group, a p-iodobenzyl group, a m-iodobenzyl group, an o-iodobenzyl group, a p-hydroxybenzyl group, a m-hydroxybenzyl group, an o-hydroxybenzyl group, a p-nitrobenzyl group, a m-nitrobenzyl group, an o-nitrobenzyl group, a p-cyanobenzyl group, a m-cyanobenzyl group, an o-cyanobenzyl group or the like can be given, for example.

As the unsubstituted heterocyclic group including 5 to 50 (preferably 5 to 30, more preferably 5 to 18) ring atoms, a pyrrolyl group, a pyrazinyl group, a pyridinyl group, an indolyl group, an isoindolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, a phenanthridinyl group, an acridinyl group, a phenanthronyl group, an a thienyl group, and a monovalent group formed from a pyridine ring, a pyrazine ring, a pyrimidine ring, a pyridazine ring, a triazine ring, an indole ring, a quinoline ring, an acridine ring, a pyrrolidine ring, a dioxane ring, a piperidine ring, a morpholine ring, a piperazine ring, a carbazole ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyran ring, a dibenzofuran ring, a benzo[a]dibenzofuran ring, a benzo[b]dibenzofuran ring, a benzo[c]dibenzofuran ring, a 1,3-benzodioxole ring, a 2,3-dihydro-1,4-benzodioxine ring, a phenanthro[4,5-bcd]furan ring, and a benzophenoxazine ring, or the like.

As the unsubstituted divalent heterocyclic group including 5 to 50 (preferably 5 to 30, more preferably 5 to 18) ring atoms, a divalent group formed of the above-exemplified monovalent heterocyclic groups, the heterocycles or the like can be given.

The substituted or unsubstituted heterocyclic group including 5 to 50 ring atoms also includes the following groups. The divalent heterocyclic group including 5 to 50 ring atoms also includes groups formed by allowing the following groups to be divalent groups.

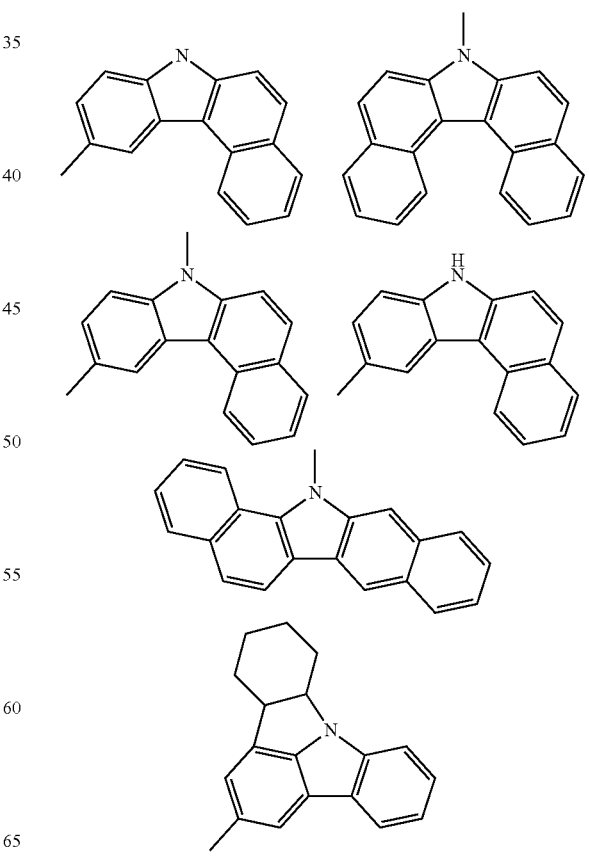

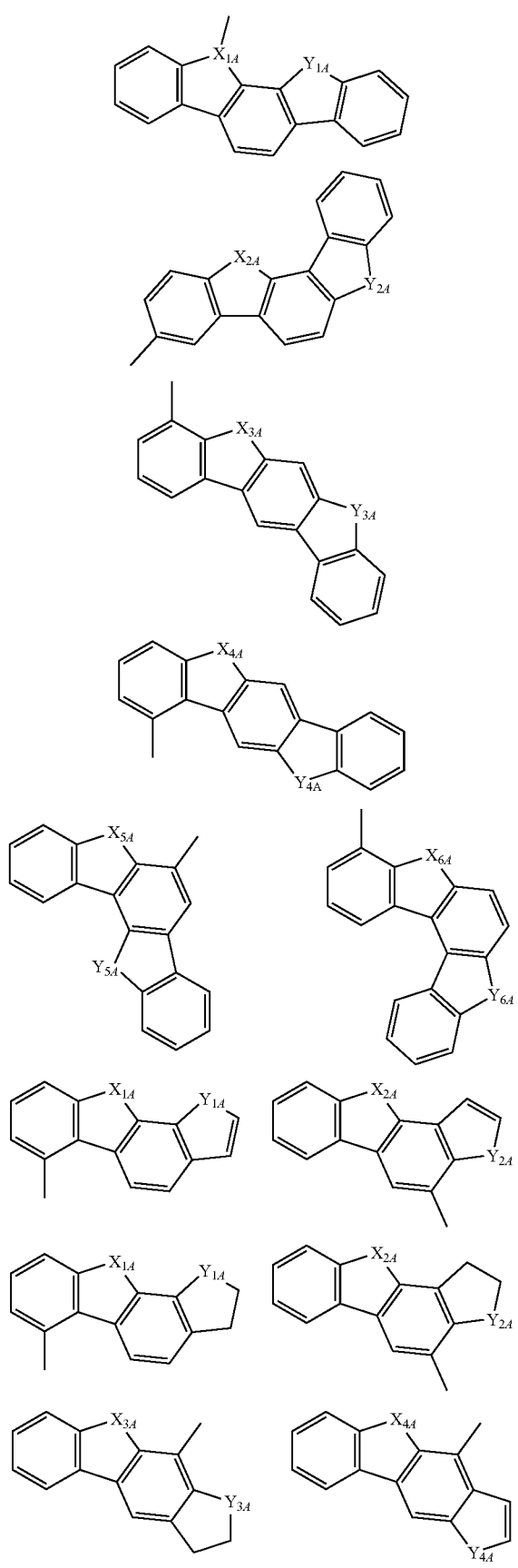
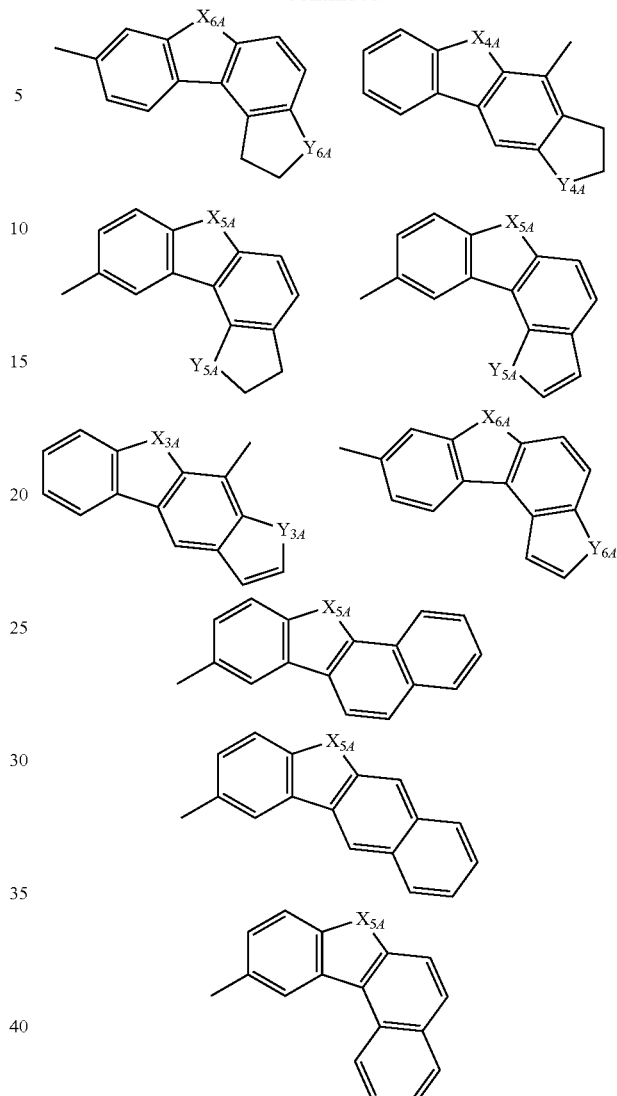

wherein $X_{1A}$ to $X_{6A}$ and $Y_{1A}$ to $Y_{6A}$ are independently an oxygen atom, a sulfur atom, a —NZ— group or —NH— group. Z is a substituted or unsubstituted aryl group including 6 to 50 ring carbon atoms, a substituted or unsubstituted heterocyclic group including 5 to 50 ring atoms or a substituted or unsubstituted alkyl group including 1 to 50 carbon atoms. If two or more Zs are present, the two or more Zs may be the same or different.

As the halogen atom, a fluorine atom, a chlorine atom, a bromine atom, an iodine atom or the like can be given.

The electroluminescence device according to one aspect of the invention comprises: an anode, a cathode and an organic layer between the anode and the cathode, the organic layer comprising an emitting layer, and at least one layer between the emitting layer and the anode, the emitting layer comprising a compound represented by the following formula (1), and at least one layer between the emitting layer and the anode comprising a compound represented by the following formula (2):

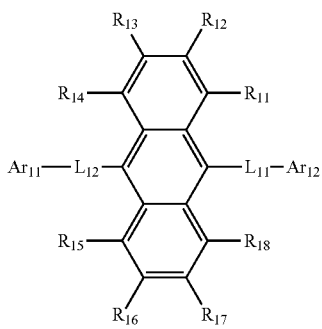

(1)

The definition of the substituents in the formula (1) will be given later.

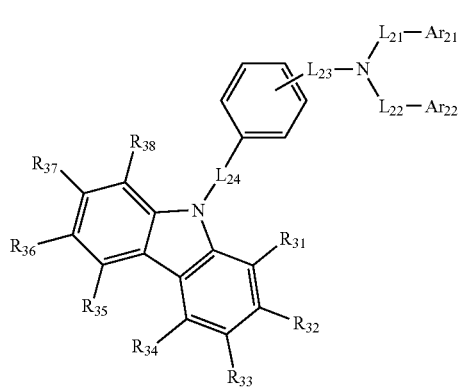

(2)

The definition of the substituents in the formula (2) will be given later.

In the specification, as for the "at least one layer between the emitting layer and the anode", when one organic layer is present between the emitting layer and the anode, the at least one layer indicates said organic layer, and when plural organic layers are present, the at least one layer indicates at least one of said plural organic layers. For example, when two or more organic layers are present between the emitting layer and the anode, an organic layer closer to the emitting layer is called a "hole-transporting layer" and an organic layer closer to the anode is called a "hole-injecting layer". The "hole-transporting layer" and the "hole-injecting layer" may respectively be one or may respectively two or more. There may be a case that one of these is a single layer and the others are two or more layers.

By using the compound represented by the formula (1) and the compound represented by the formula (2) in a prescribed organic layer, the luminous efficiency of an organic EL device can be improved.

An explanation will be made on the compound represented by the formula (1) (hereinafter often referred to as the compound (1)). The compound (1) is contained in the emitting layer.

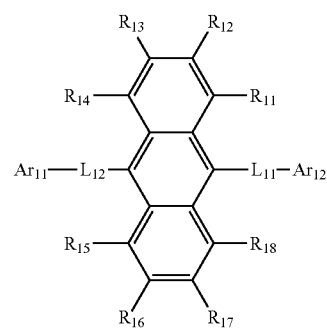

(1)

wherein in the formula (1),
$R_{11}$ to $R_{18}$ are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group having 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{101}$)($R_{102}$)($R_{103}$), —C(=O)$R_{104}$, —COO$R_{105}$, —N($R_{106}$)($R_{107}$), a halogen atom,
a cyano group, a nitro group,
a substituted or unsubstituted aryl group including 6 to 50 ring carbon atoms, or a substituted or unsubstituted heterocyclic group including 5 to 50 ring atoms,
$R_{101}$ to $R_{107}$ are independently a hydrogen atom, a substituted or unsubstituted alkyl group including 1 to 50 carbon atoms, a substituted or unsubstituted aryl group including 6 to 50 ring carbon atoms or a substituted or unsubstituted heterocyclic group including 5 to 50 ring atoms,
when two or more $R_{101}$ to $R_{107}$ are present, the two or more of each of $R_{101}$ to $R_{107}$ may be the same or different,
at least one of $Ar_{11}$ and $R_{12}$ is a monovalent group represented by the following formula (11):

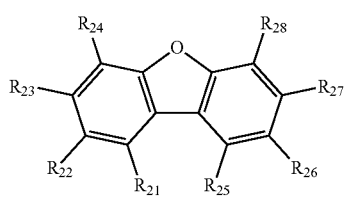

(11)

wherein the formula (11),
one of $R_{21}$ to $R_{28}$ is a single bond bonding to $L_{11}$ or $L_{12}$,
$R_{21}$ to $R_{28}$ that do not bond to $L_{11}$ or $L_{12}$ are independently a hydrogen atom, an alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{101}$)($R_{102}$)($R_{103}$), —C(=O)$R_{104}$, —COO$R_{105}$, —N($R_{106}$)($R_{107}$), a halogen atom, a cyano group, a nitro group, a substituted or unsubstituted aryl group including 6 to 50 ring carbon atoms or a substituted or unsubstituted heterocyclic group including 5 to 50 ring atoms, $R_{101}$ to $R_{107}$ are as defined as above, $Ar_{11}$ or $Ar_{12}$ that are not a monovalent group represented by the formula (11) is a substituted or unsubstituted aryl group including 6 to 50 ring carbon atoms, $L_{11}$ and $L_{12}$ are independently a single bond, a substituted or unsubstituted alkylene group including 1 to 50 carbon atoms, a substituted or unsubstituted arylene group including 6 to 50 ring carbon atoms or a substituted or unsubstituted divalent heterocyclic group including 5 to 50 ring atoms.

In one embodiment, it is preferred that $R_{21}$ or $R_{22}$ in the formula (1) is a single bond bonding to $L_{11}$, and it is more preferred that $R_{22}$ is a single bond bonding to $L_{11}$ in the formula (1).

In one embodiment, it is preferred that $L_{11}$ in formula (1) be a single bond.

In one embodiment, it is more preferred that $R_{21}$ to $R_{28}$ that do not bond to $L_{11}$ be independently a hydrogen atom or a substituted or unsubstituted alkyl group including 1 to 50 carbon atoms. It is more preferred that all be hydrogen atoms.

In one embodiment, it is preferred that $R_{11}$ to $R_{18}$ in the formula (1) be independently a hydrogen atom or a substituted or unsubstituted alkyl group including 1 to 50 carbon atoms. It is preferred that all be hydrogen atoms.

In one embodiment, the compound (1) is a compound represented by the following formula (1-1):

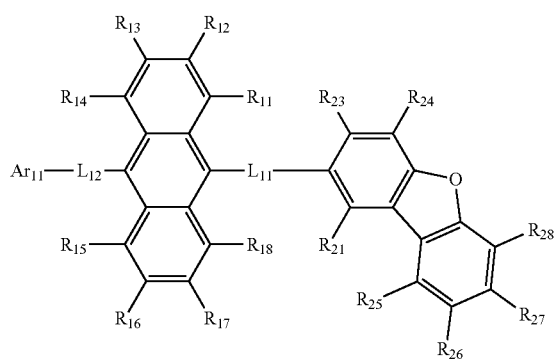

(1-1)

In the formula (1-1), $R_{11}$ to $R_{18}$, $Ar_{11}$, $L_{11}$, $L_{12}$, $R_{21}$ and $R_{23}$ to $R_{28}$ are as defined in the formula (1).

In one embodiment, the compound (1) is a compound represented by the following formula (1-2):

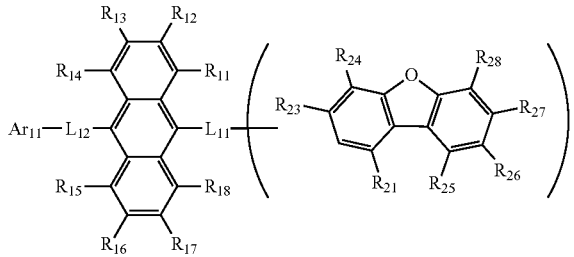

(1-2)

In the formula (1-2), $L_{11}$ is a single bond, $R_{11}$ to $R_{18}$, $Ar_{11}$, $L_{12}$ and $R_{21}$ to $R_{28}$ are as defined in the formula (1).

In one embodiment, the compound (1) is a compound represented by the following formula (1-3):

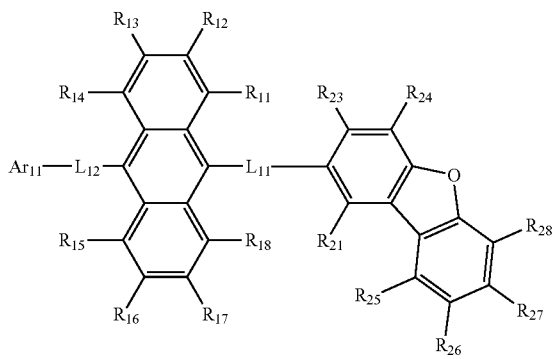

(1-3)

In the formula (1-3), $L_{11}$ is a single bond, $R_{11}$ to $R_{18}$, $Ar_{11}$, $L_{12}$, $R_{21}$ and $R_{23}$ to $R_{28}$ are as defined in the formula (1).

In one embodiment, in the above-mentioned formulas (1), (1-1), (1-2) and (1-3), it is preferred that $R_{21}$ to $R_{28}$ that do not bond to $L_{11}$ be a hydrogen atom.

In one embodiment, in the above-mentioned formulas (1), (1-1), (1-2) and (1-3), it is preferred that $R_{11}$ to $R_{18}$ be a hydrogen atom.

In one embodiment, the compound (1) is a compound represented by the following formula (1-4).

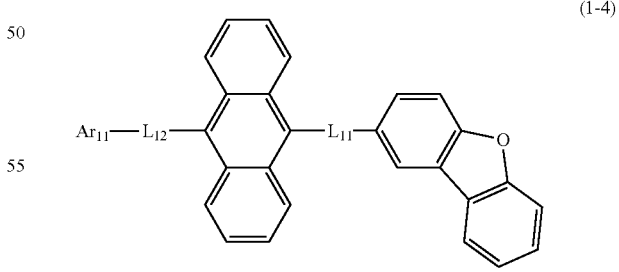

(1-4)

In the formula (1-4), $L_{11}$ is a single bond, and $Ar_1$ and $L_{12}$ are as defined in the formula (1).

As the substituent in the "substituted or unsubstituted" in the compounds (1), (1-1), (1-2), (1-3) and (1-4) (hereinbelow, often referred to as an "arbitrary substituent" in the compound (1)", for example, an alkyl group including 1 to 50 carbon atoms, an alkenyl group including 2 to 50 carbon atoms, an alkynyl group including 2 to 50 carbon atoms, a cycloalkyl group including 3 to 50 ring carbon atoms, an alkoxy group including 1 to 50 carbon atoms, an alkylthio group including 1 to 50 carbon atoms, an aryloxy group including 6 to 50 ring carbon atoms, an arylthio group including 6 to 50 ring carbon atoms, an aralkyl group including 7 to 50 carbon atoms, —Si($R_{41}$)($R_{42}$)($R_{43}$), —C(=O)$R_{44}$, —COO$R_{45}$, —S(=O)$_2$$R_{46}$, —P(=O)($R_{47}$)($R_{48}$), —Ge($R_{49}$)($R_{50}$)($R_{51}$), —N($R_{52}$)($R_{53}$) (wherein $R_{41}$ to $R_{53}$ are independently a hydrogen atom, an alkyl group including 1 to 50 carbon atoms, an aryl group including 6 to 50 ring carbon atoms or a heterocyclic group including 5 to 50 ring atoms. When two or more $R_{41}$ to $R_{53}$ are present, the two or more of each of $R_{41}$ to $R_{53}$ may be the same or different), a hydroxy group, a halogen atom, a cyano group, a nitro group, an aryl group including 6 to 50 ring carbon atoms, a heterocyclic group including 5 to 50 ring atoms, or the like can be given. Among these, an alkyl group including 1 to 50 carbon atoms, an aryl group including 6 to 50 ring carbon atoms or a heterocyclic group including 5 to 50 ring atoms is preferable, with an alkyl group including 1 to 18 carbon atoms, an aryl group including 6 to 18 ring carbon atoms or a heterocyclic group including 5 to 18 ring atoms being more preferable.

Specific examples of each substituent of the compounds (1), (1-1), (1-2), (1-3) and (1-4), the arbitrary substituent and the halogen atom are the same as those given above.

As the specific examples of the compound (1), the following compounds shown below can be given.

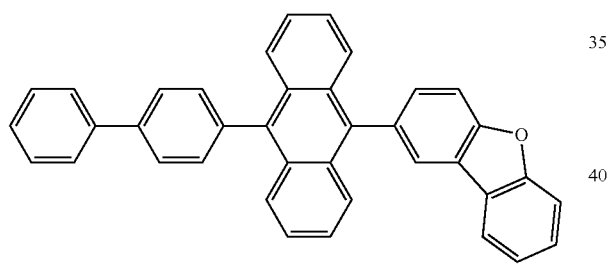

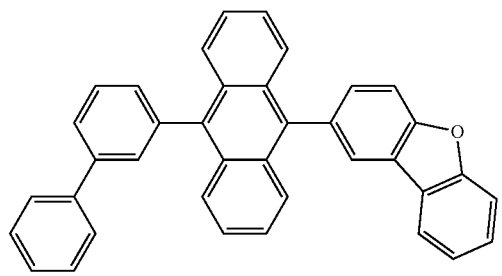

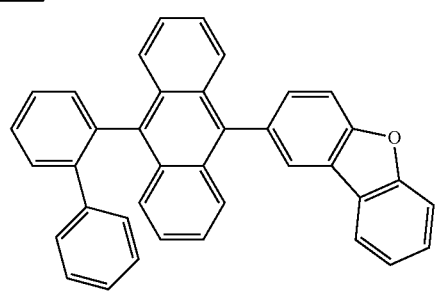

-continued

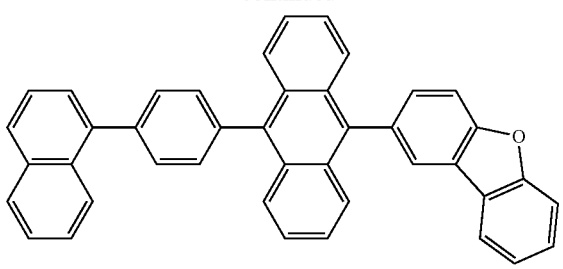

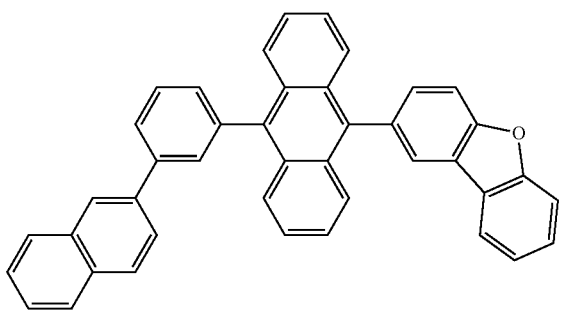

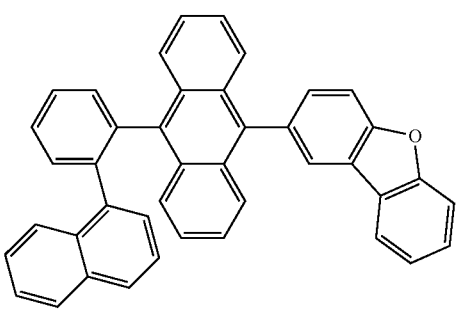

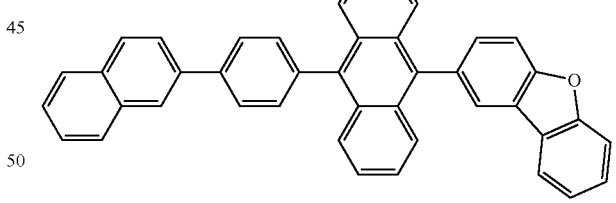

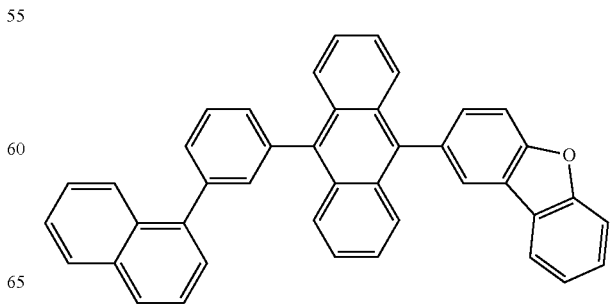

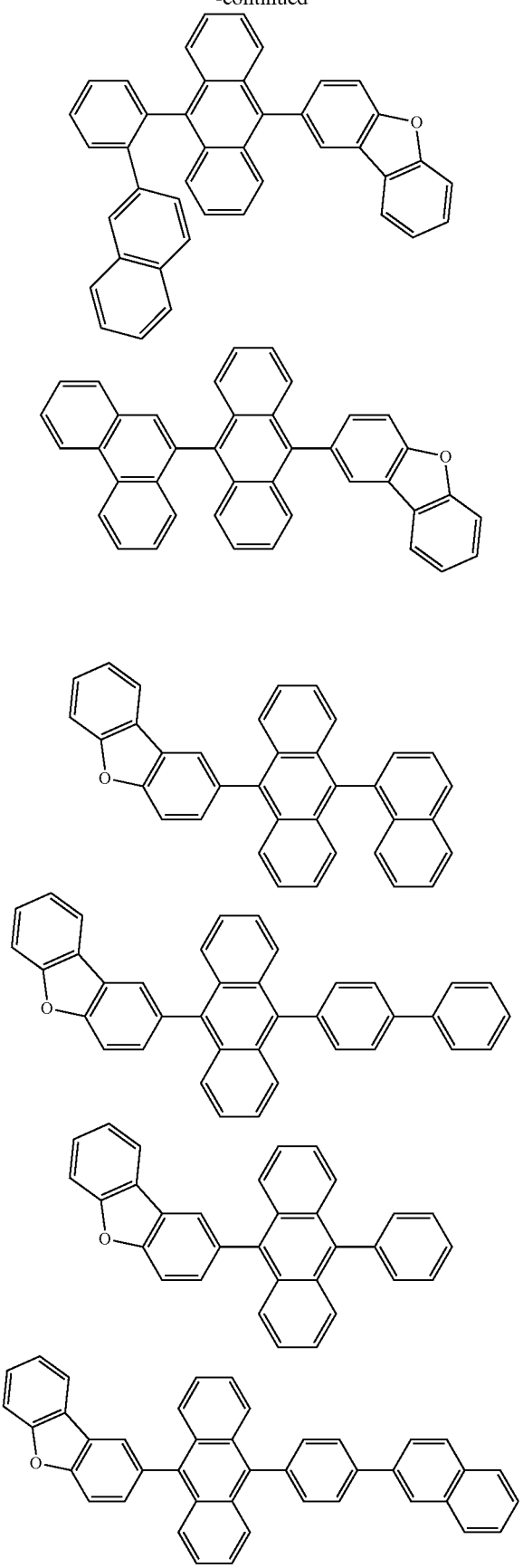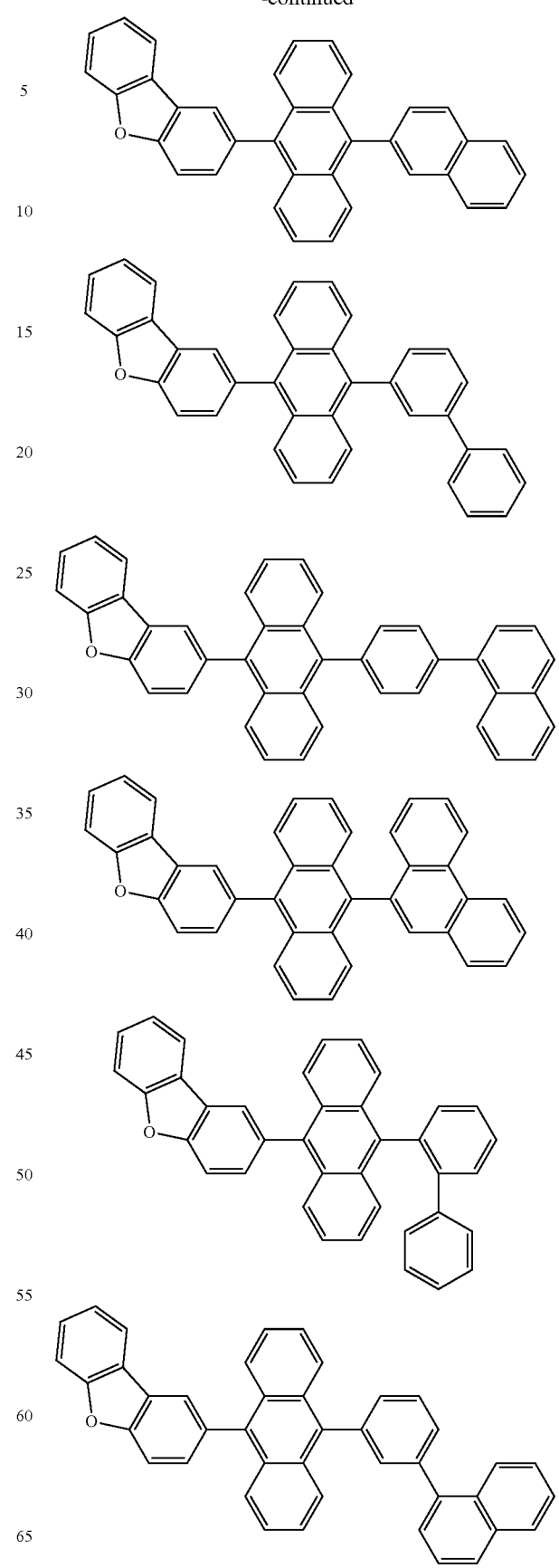

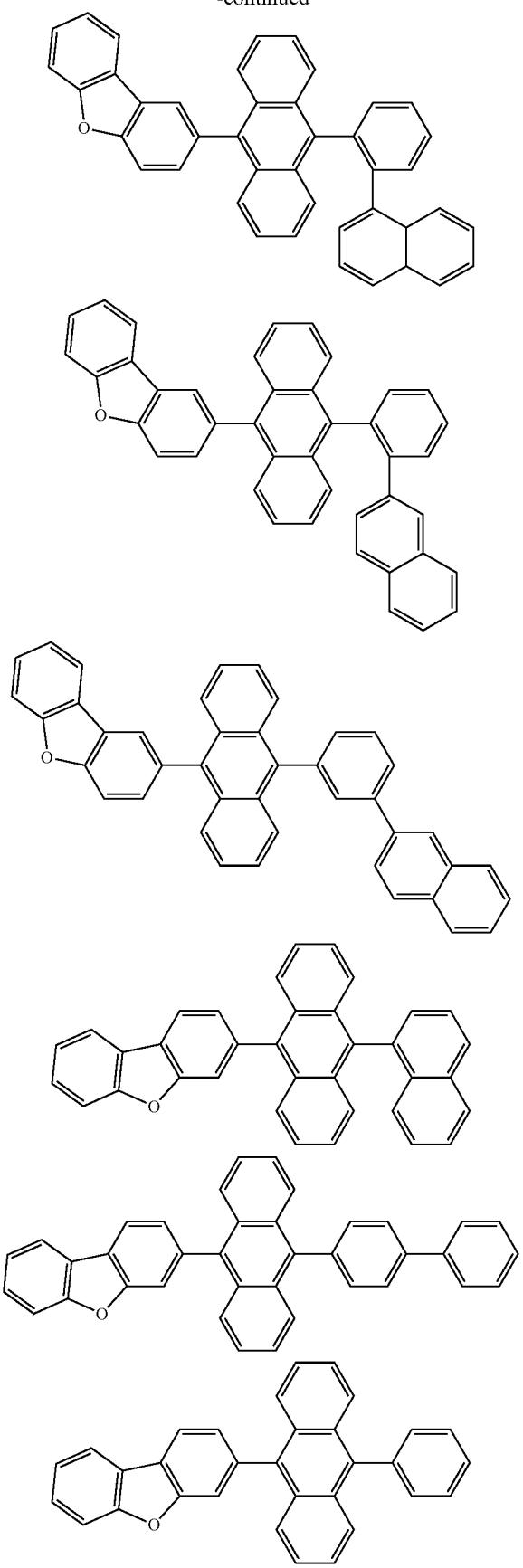
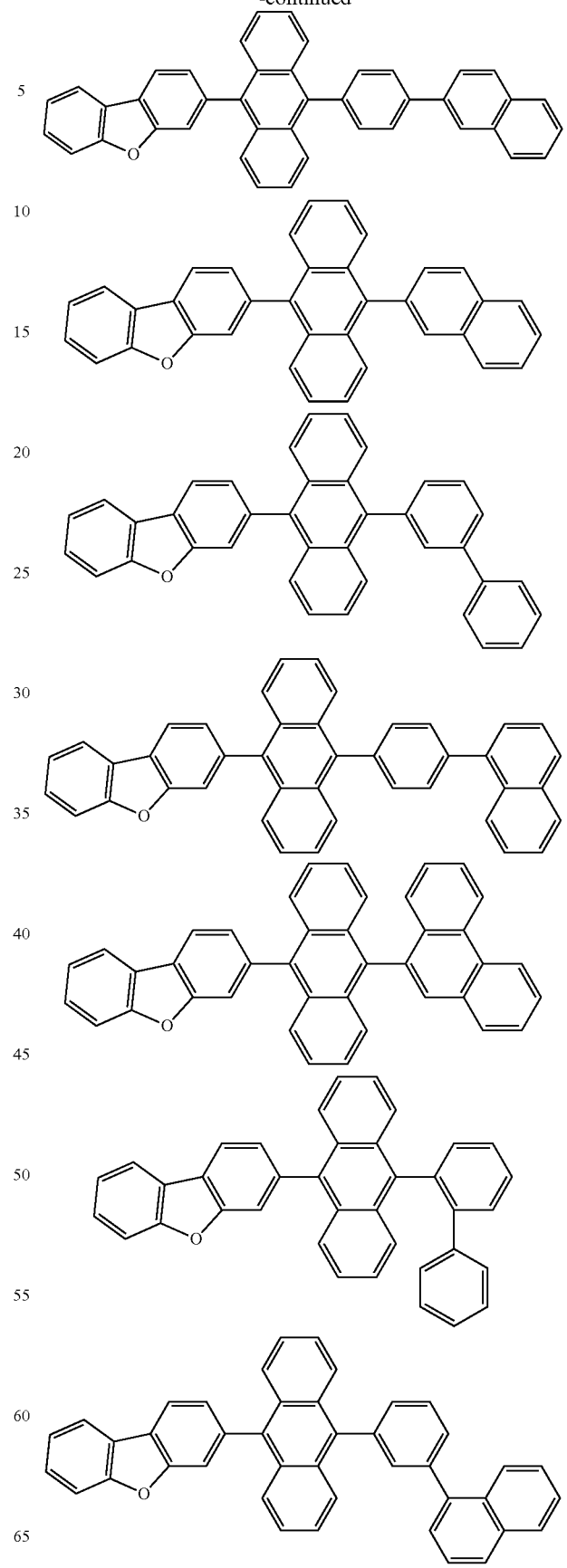

-continued
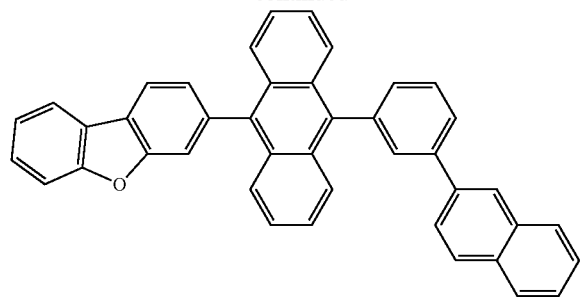
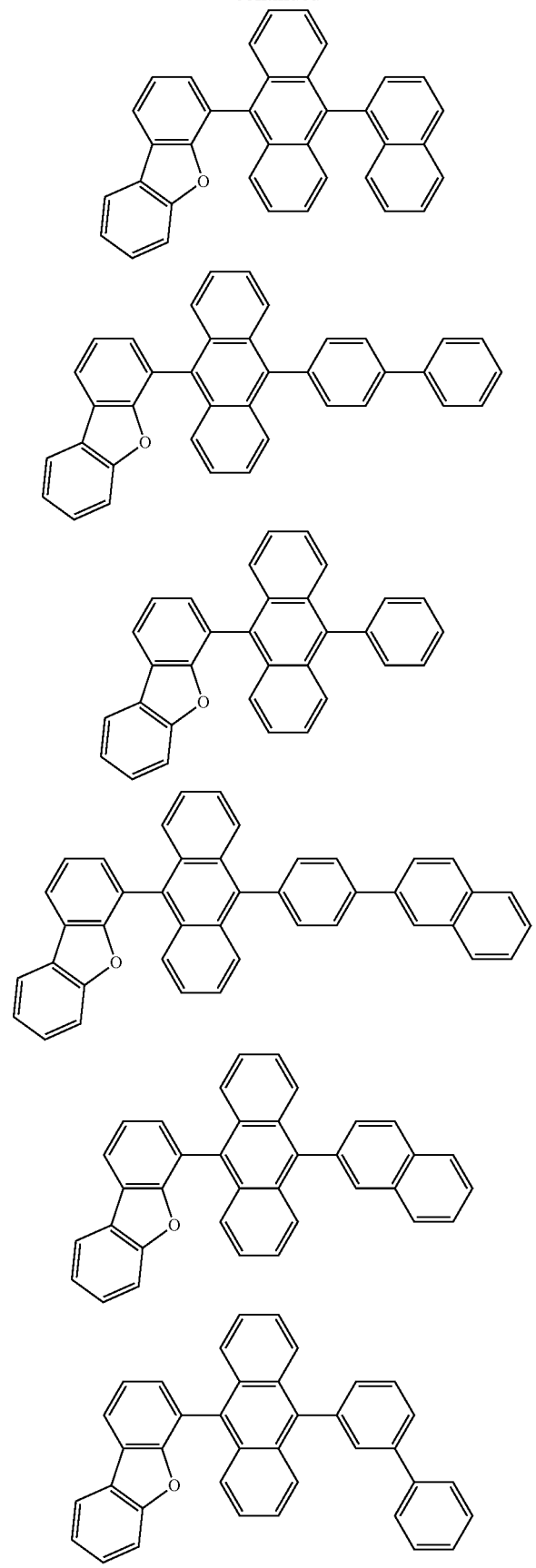

-continued
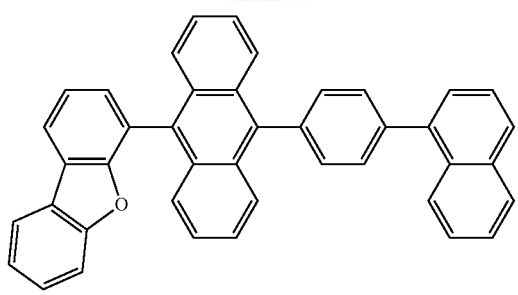
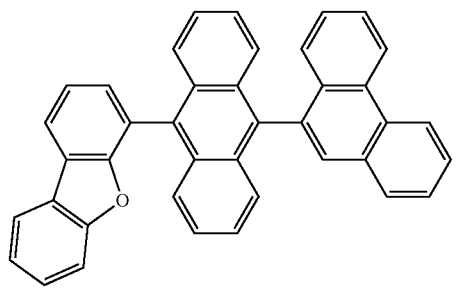
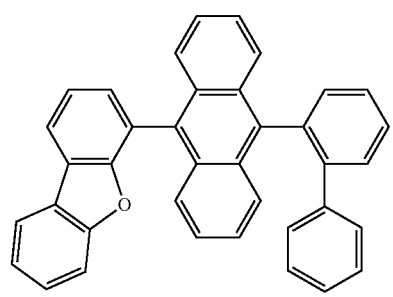
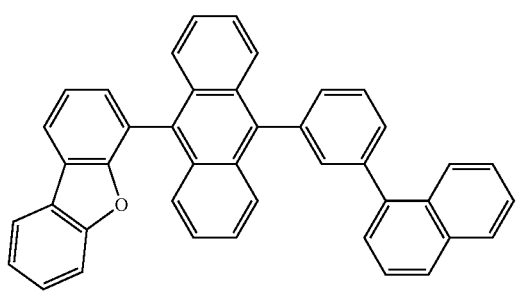
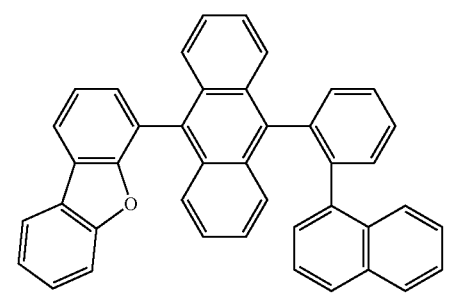
-continued
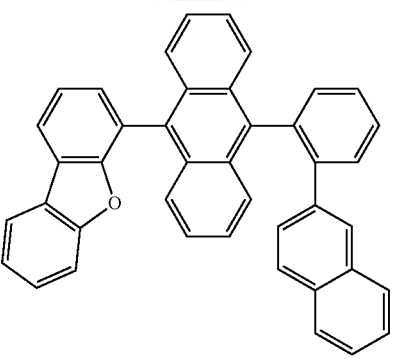
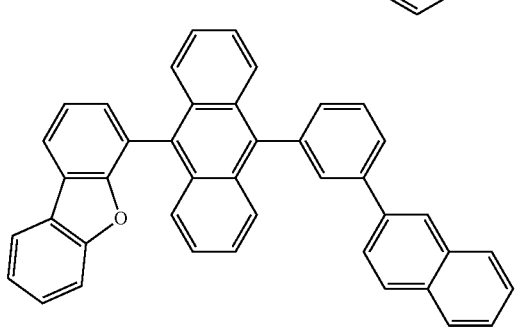
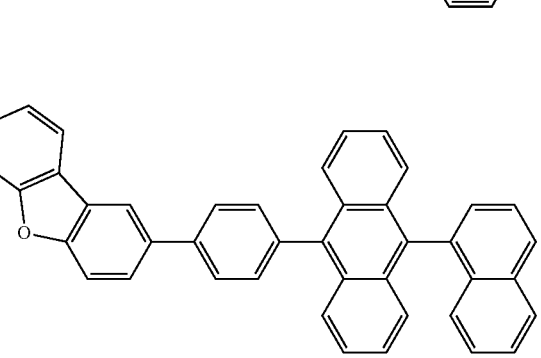
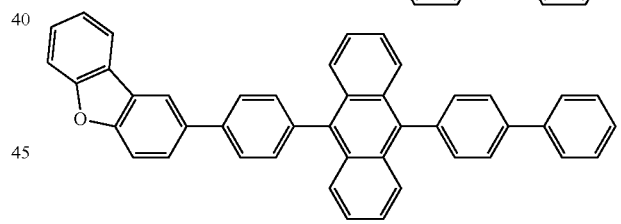
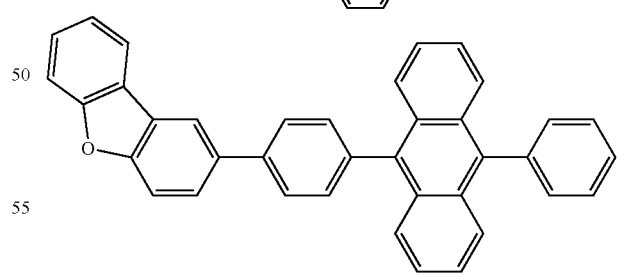
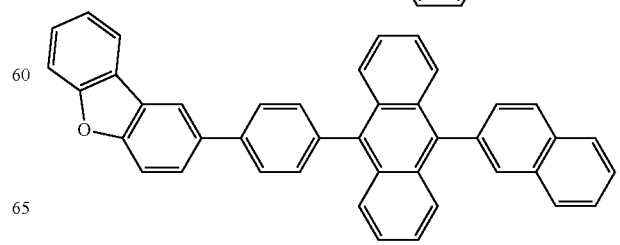

25
-continued
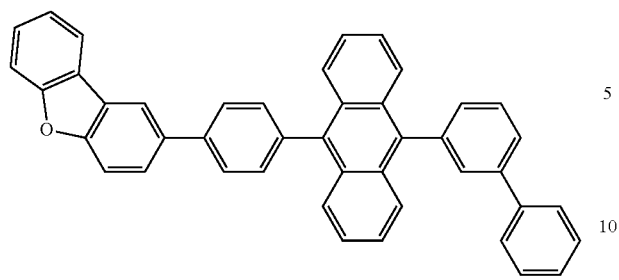
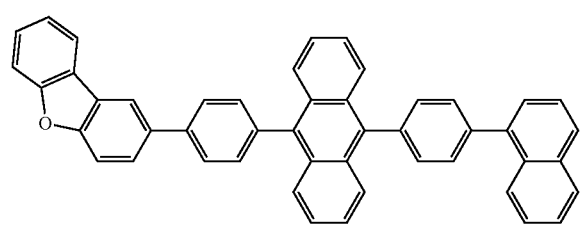
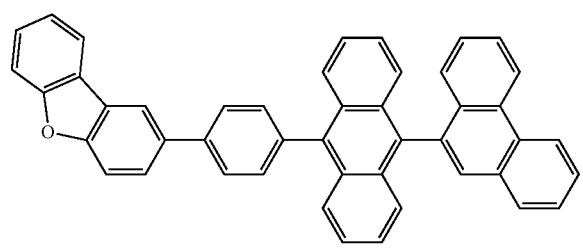
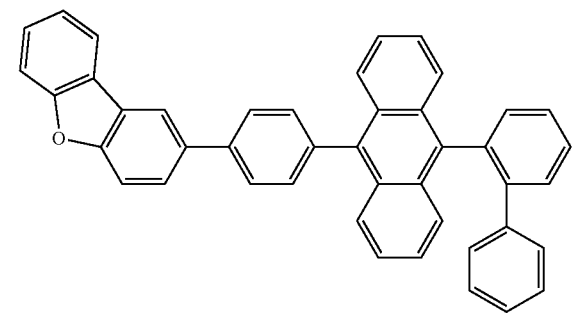
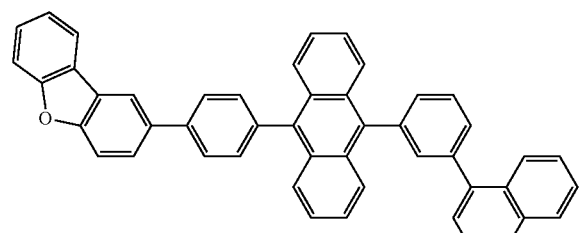
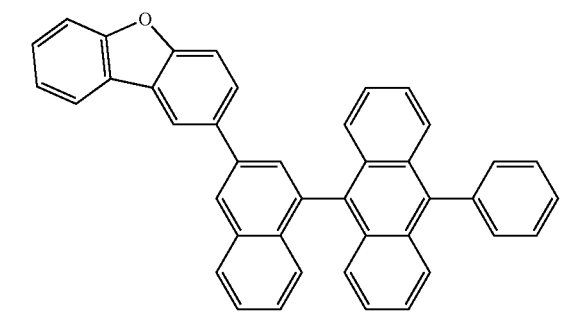
26
-continued
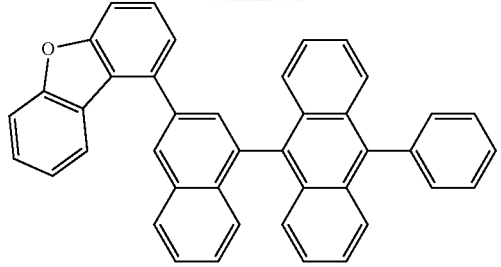
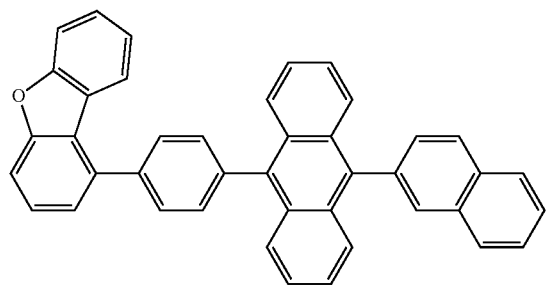
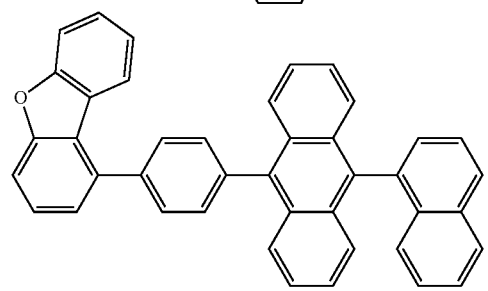
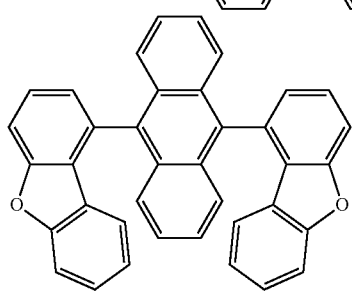
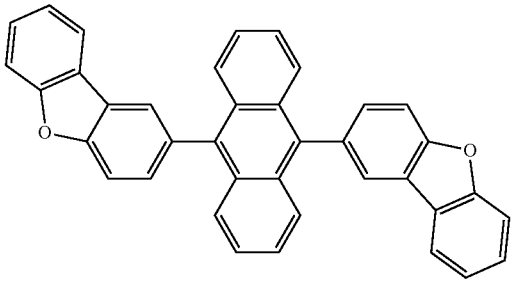
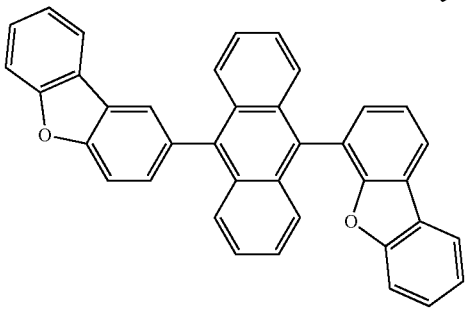

Next, an explanation will be made on the compound represented by the formula (2) (hereinafter often referred to as the compound (2)). The compound (2) is contained in at least one organic layer between the emitting layer and the anode.

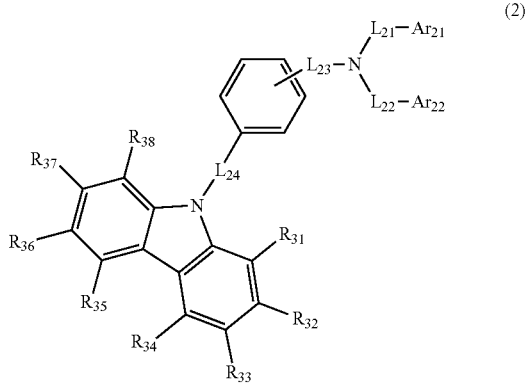

(2)

wherein in the formula (2), one or more pairs of adjacent two or more groups of $R_{31}$ to $R_{38}$ may form a substituted or unsubstituted saturated or unsaturated ring, and $R_{31}$ to $R_{38}$ that do not involve the ring formation are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, an alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{201}$)($R_{202}$)($R_{203}$), —C(=O)$R_{204}$, —COO$R_{205}$, a halogen atom, a cyano group, a nitro group, a substituted or unsubstituted aryl group including 6 to 50 ring carbon atoms or a substituted or unsubstituted heterocyclic group including 5 to 50 ring atoms, $R_{201}$ to $R_{205}$ are independently a hydrogen atom, a substituted or unsubstituted alkyl group including 1 to 50 carbon atoms, a substituted or unsubstituted aryl group including 6 to 50 ring carbon atoms or a substituted or unsubstituted heterocyclic group including 5 to 50 ring atoms, when two or more $R_{201}$ to $R_{205}$ are present, the two or more of each of $R_{201}$ to $R_{205}$ may be the same or different, $L_{21}$ to $L_{24}$ are independently a single bond, a substituted or unsubstituted alkylene group including 1 to 50 carbon atoms, a substituted or unsubstituted arylene group including 6 to 50 ring carbon atoms or a substituted or unsubstituted divalent heterocyclic group including 5 to 50 ring atoms; and $Ar_{21}$ and $Ar_{22}$ are independently a substituted or unsubstituted aryl group including 6 to 50 ring carbon atoms or a substituted or unsubstituted heterocyclic group including 5 to 50 ring atoms.

In the compound (2), $L_{23}$ and $L_{24}$ bond to the benzene ring at any of an ortho(o), meth(m) and para(p) positions. It is preferred that $L_{23}$ and $L_{24}$ bond to an ortho or meth position, with a meth position being particularly preferable.

An explanation will be made on "one or more pairs formed of adjacent two or more groups of $R_{31}$ to $R_{38}$ in the compound represented by the formula (2) may form a substituted or unsubstituted saturated or unsaturated ring".

The "one pair formed of adjacent two or more groups of $R_{31}$ to $R_{38}$" is, for example, combination of $R_{31}$ and $R_{32}$, $R_{32}$ and $R_{33}$, $R_{33}$ and $R_{34}$, $R_{34}$ and $R_{35}$, $R_{35}$ and $R_{36}$, $R_{36}$ and $R_{37}$, $R_{37}$ and $R_{38}$, $R_{31}$ and $R_{32}$ and $R_{33}$, $R_{32}$ and $R_{33}$ and $R_{34}$, or the like.

The substituents of the "substituted or unsubstituted" for the above-mentioned saturated or unsaturated ring are as explained later with reference to the formula (2).

The "saturated or unsaturated ring" means, when a ring is formed by $R_{31}$ and $R_{32}$, a ring formed by a carbon atom to which $R_{31}$ bonds, a carbon atom to which $R_{32}$ bonds and one or more arbitrary elements. Specifically, when a ring is formed by $R_{31}$ and $R_{32}$, if a ring is formed by a carbon atom to which $R_{31}$ bonds, a carbon atom to which $R_{32}$ bonds and four carbon atoms, a ring formed by $R_{31}$ and $R_{32}$ is a benzene ring.

The "arbitrary element" is preferably a C element, an N element, an O element and a S element. If an arbitrary element is a C element or an N element, an atomic bonding which does not involve the ring formation may be terminated by a hydrogen atom or the like.

The "one or more arbitrary elements" are preferably 2 or more and 15 or less, more preferably 3 or more and 12 or less and further preferably 3 or more and 5 or less arbitrary elements.

When one pair of $R_{32}$ and $R_{33}$ and $R_{34}$ forms a ring, the compound represented by the formula (2) is a compound represented by the following formula (2-10), for example. Further, in the following formula (2-10), when $R_{61}$ is a phenyl group, one pair of $R_{32}$ and $R_{33}$ and $R_{34}$ forms a substituted ring.

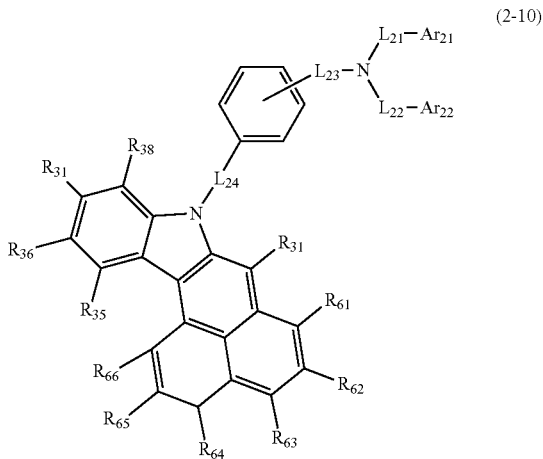

(2-10)

wherein in the formula (2-10), $R_{31}$, $R_{35}$ to $R_{38}$, $L_{21}$ to $L_{24}$, $Ar_{21}$ and $Ar_{22}$ are as defined in the formula (2), and $R_{61}$ to $R_{66}$ have the same meaning as that of the substituent in the "substituted or unsubstituted" in the compound (2) (arbitrary substituent in the compound (2)) mentioned later.

The "one or more pairs" means, for example, that $R_{31}$ and $R_{32}$ may form a ring and simultaneously $R_{37}$ and $R_{38}$ may form a ring. In this case, the compound represented by the formula (2) is a compound represented by the following formula (2-11), for example. In the following formula (2-11), when $R_{71}$ is a phenyl group, for example, $R_{31}$ and $R_{32}$ form a substituted ring.

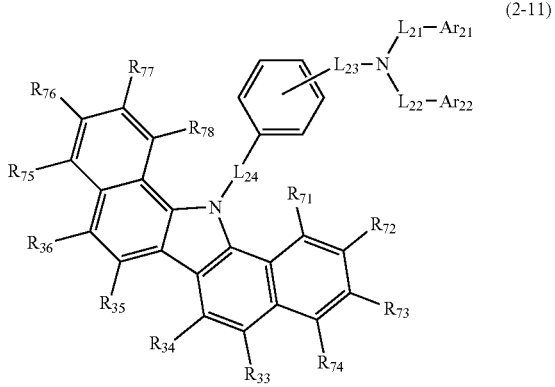

(2-11)

wherein in the formula (2-11), $R_{33}$ to $R_{36}$, $L_{21}$ to $L_{24}$, $Ar_{21}$ and $Ar_{22}$ are as defined in the above-mentioned formula (2), and $R_{71}$ to $R_{78}$ have the same meaning as that of the substituent in the case of the "substituted or unsubstituted" in the formula (2) (arbitrary substituent of the compound (2)) mentioned later.

In one embodiment, it is preferred that the compound (2) comprises one or both of the compound represented by the following formula (2a) and the compound represented by the following formula (2b) (hereinbelow, referred to as the compounds (2a) and (2b)).

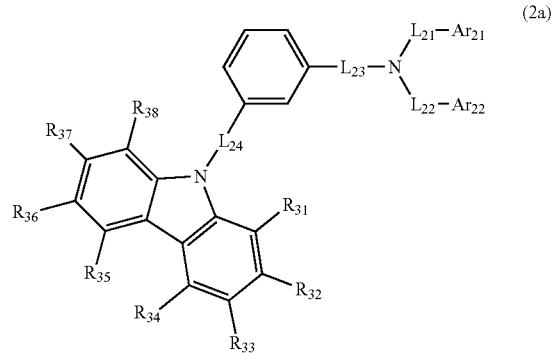

(2a)

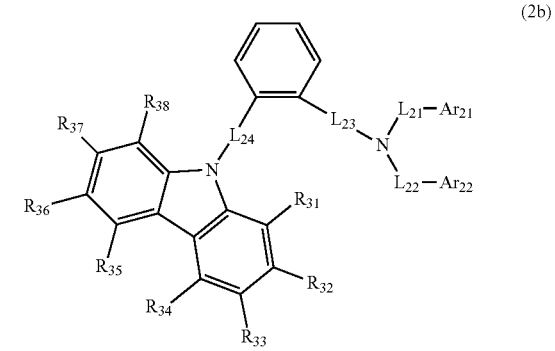

(2b)

wherein in the formulas (2a) and (2b), $R_{31}$ to $R_{38}$, $L_{21}$ to $L_{24}$, $Ar_{21}$ and $Ar_{22}$ are as defined in the above-mentioned formula (2).

In one embodiment, it is preferred that the compound (2) be the compound (2a), i.e. $L_{23}$ and $L_{24}$ bond to the benzene ring at the meth position to each other.

In one embodiment, it is preferred that $L_{24}$ in the compound (2) be a single bond.

In one embodiment, it is preferred that $L_{23}$ in the compound (2) be a single bond.

In one embodiment, it is preferred that one of $Ar_{21}$ and $Ar_{22}$ in the compound (2) be a substituted or unsubstituted aryl group including 6 to 50 ring carbon atoms and the other be a substituted or unsubstituted aryl group including 6 to 50 ring carbon atoms or a substituted or unsubstituted heterocyclic group including 5 to 50 ring atoms.

In one embodiment, it is preferred that $R_{31}$ to $R_{38}$ in the compound (2) be a hydrogen atom.

In one embodiment, the compound (2) is a compound represented by the following formula (2a-1) and/or a compound represented by the following compound (2b-1).

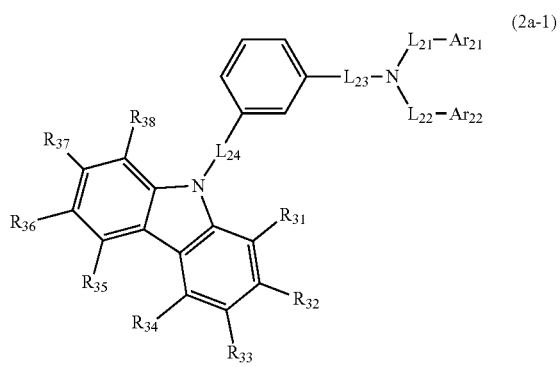

(2a-1)

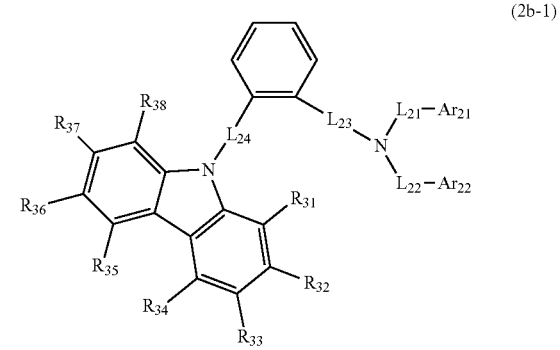

(2b-1)

wherein in the formulas (2a-1) and (2b-1), $L_{24}$ is a single bond, and $R_{31}$ to $R_{38}$, $L_{21}$ to $L_{23}$, $Ar_{21}$ and $Ar_{22}$ are as defined in the formula (2).

In one embodiment, the compound (2) is a compound represented by the following formula (2a-2) and/or a compound represented by the following formula (2b-2).

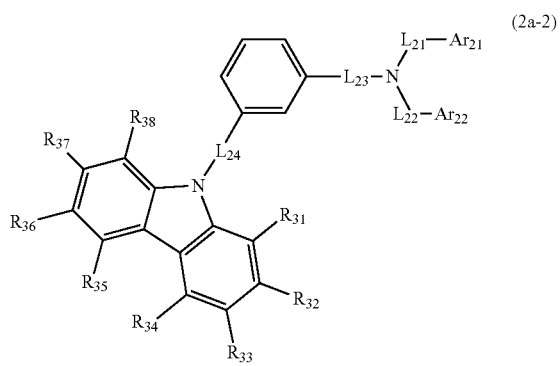

(2a-2)

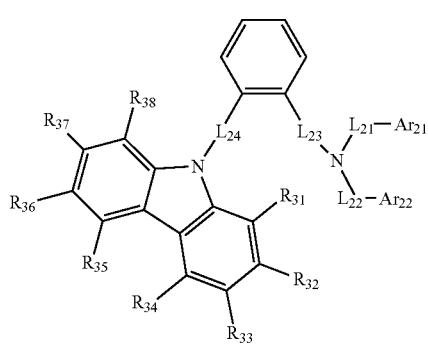

wherein in the formulas (2a-2) and (2b-2), $L_{23}$ is a single bond, and $R_{31}$ to $R_{38}$, $L_{21}$, $L_{22}$, $L_{24}$, $Ar_{21}$ and $Ar_{22}$ are as defined in the formula (2).

In one embodiment, the compound (2) is a compound represented by the following formula (2a-3) and/or a compound represented by the following formula (2b-3).

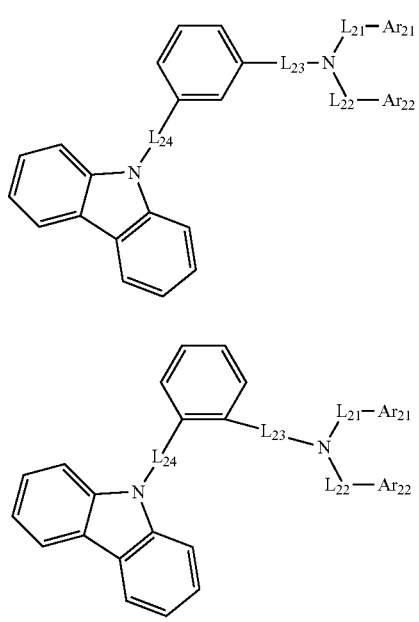

wherein in the formulas (2a-3) and (2b-3), $L_{21}$ to $L_{24}$, $Ar_{21}$ and $Ar_{22}$ are as defined in the formula (2).

In one embodiment, the compound (2) is a compound represented by the following formula (2a-4):

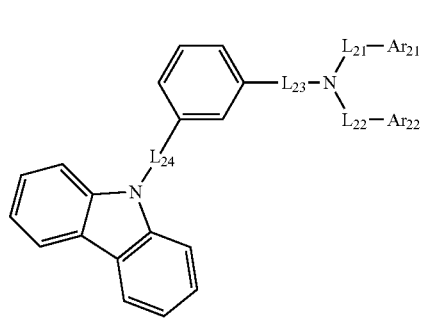

wherein in the formula (2a-4), $L_{23}$ is a single bond and $L_{21}$, $L_{22}$, $L_{24}$, $Ar_{21}$ and $Ar_{22}$ are as defined in the formula (2).

As the substituent in the "substituted or unsubstituted" in the formula (2), (2a), (2b), (2a-1), (2b-1), (2a-2), (2b-2), (2a-3), (2b-3) and (2a-4) (hereinbelow, often referred to as an "arbitrary substituent" in the compound (2)), for example, an alkyl group including 1 to 50 carbon atoms, an alkenyl group including 2 to 50 carbon atoms, an alkynyl group including 2 to 50 carbon atoms, a cycloalkyl group including 3 to 50 ring carbon atoms, an alkoxy group including 1 to 50 carbon atoms, an alkylthio group including 1 to 50 carbon atoms, an aryloxy group including 6 to 50 ring carbon atoms, an arylthio group including 6 to 50 ring carbon atoms, an aralkyl group including 7 to 50 carbon atoms, —Si($R_{41}$)($R_{42}$)($R_{43}$), —C(=O)$R_{44}$, —COO$R_{45}$, —S(=O)$_2R_{46}$, —P(=O)($R_{47}$)($R_{48}$), —Ge($R_{49}$)($R_{50}$)($R_{51}$) (wherein $R_{41}$ to $R_{51}$ are independently a hydrogen atom, an alkyl group including 1 to 50 carbon atoms, an aryl group including 6 to 50 ring carbon atoms or a heterocyclic group including 5 to 50 ring atoms, when two or more $R_{41}$ to $R_{51}$ are present, the two or more of each of $R_{41}$ to $R_{51}$ may be the same or different), a hydroxy group, a halogen atom, a cyano group, a nitro group, an aryl group including 6 to 50 ring carbon atoms, a heterocyclic group including 5 to 50 ring atoms or the like can be given. Among these, an alkyl group including 1 to 50 carbon atoms, an aryl group including 6 to 50 ring carbon atoms or a heterocyclic group including 5 to 50 ring atoms are preferable, with an alkyl group including 1 to 18 carbon atom, an aryl group including 6 to 18 carbon atoms or a heterocyclic group including 5 to 18 ring atoms being more preferable.

The specific examples of each substituent, the arbitrary substituent and the halogen atom in the compound (2) are the same as those mentioned above. Each substituent and the arbitrary substituent in the compound (2) do not comprise a substituted or unsubstituted amino group. Therefore, in the compound (2), the number of the amino group is only one.

As specific examples of the compound (2), the following compounds can be given, for example.

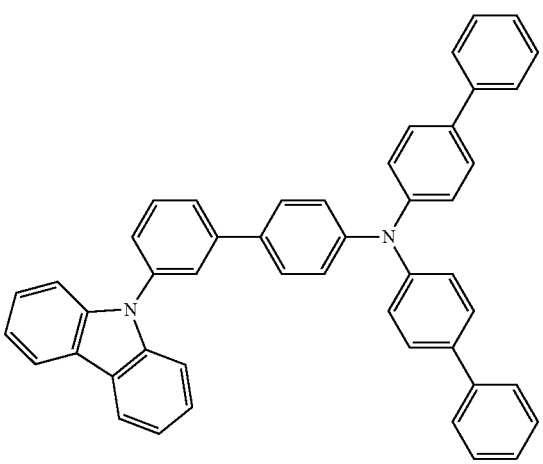

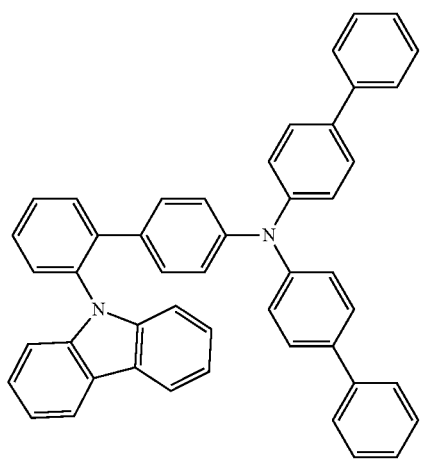
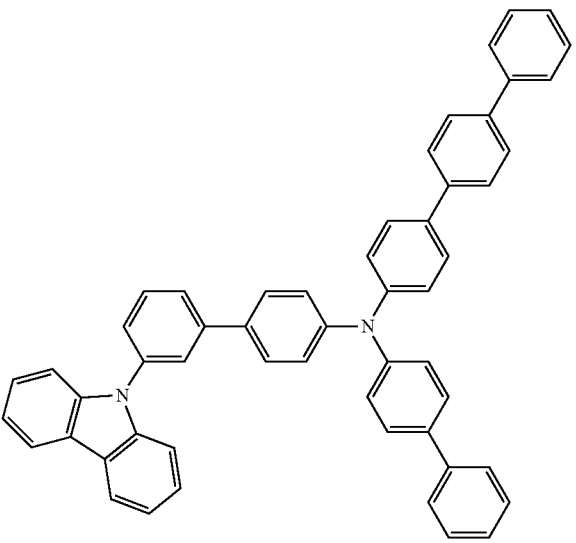
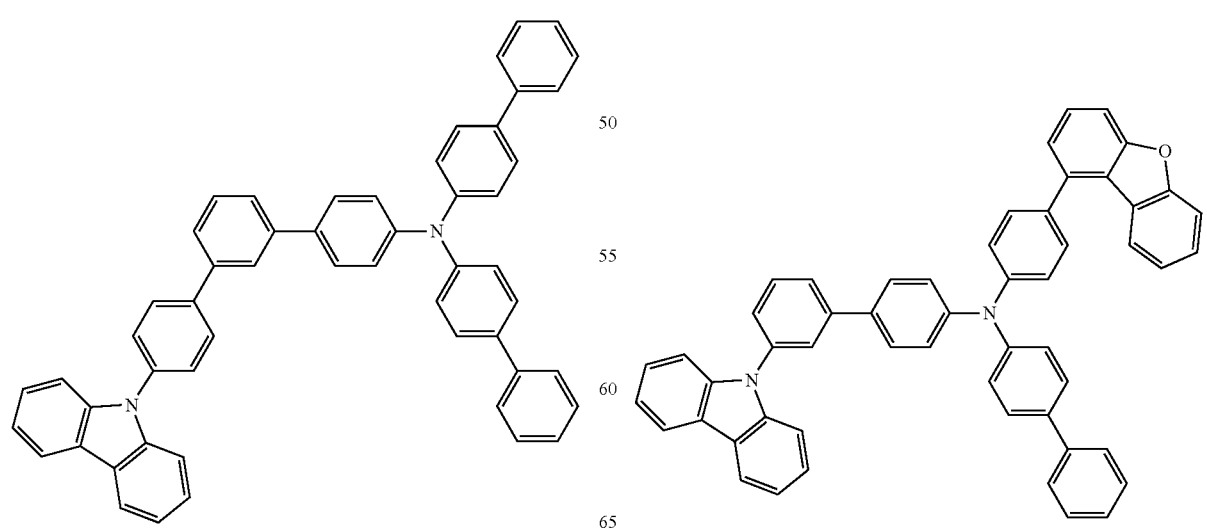

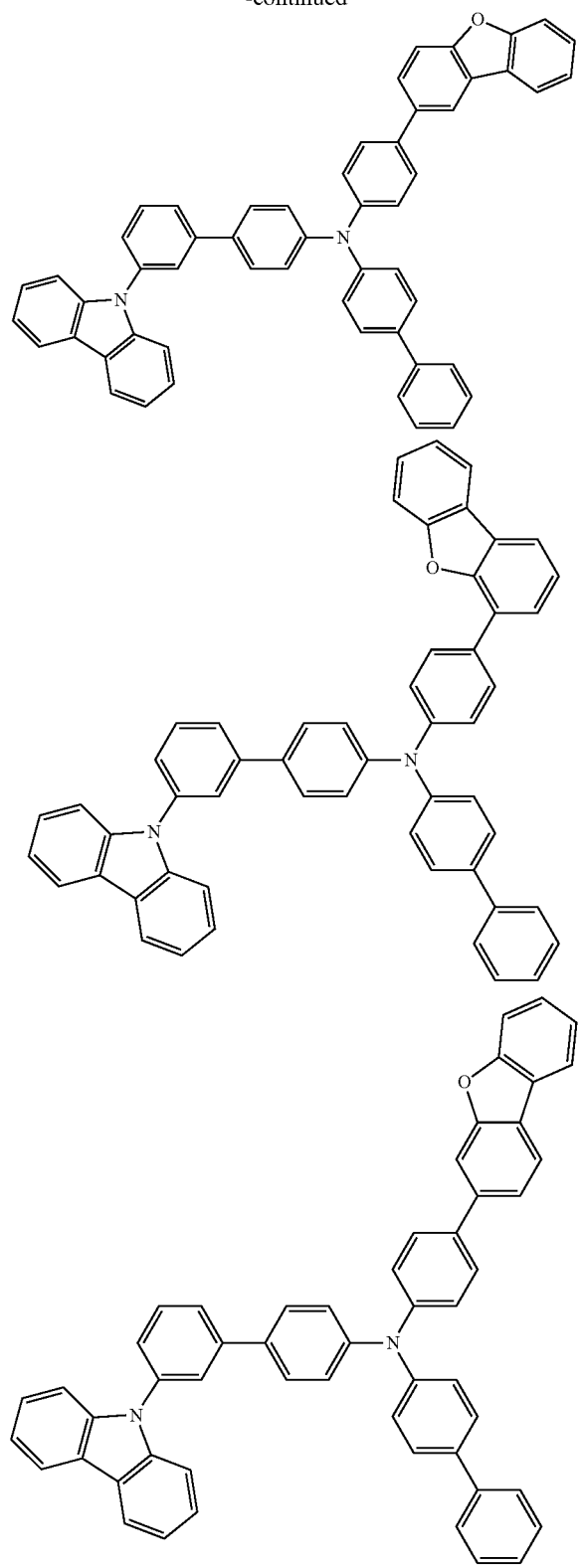

In one embodiment, the compound represented by the formula (1) contained in the emitting layer is a compound represented by the above formula (1-1), and the compound represented by the formula (2) contained in at least one layer between the emitting layer and the anode comprises any one or both of the compound represented by the formula (2a) and the compound represented by the formula (2b).

In one embodiment, the compound represented by the formula (1) contained in the emitting layer is a compound represented by the above formula (1-1), and the compound represented by the formula (2) contained in at least one layer between the emitting layer and the anode comprises any one or both of the compound represented by the formula (2a-1) and the compound represented by the formula (2b-1).

In one embodiment, the compound represented by the formula (1) contained in the emitting layer is a compound represented by the above formula (1-2), and the compound represented by the formula (2a) and the compound represented by the formula (2b) contained in at least one layer between the emitting layer and the anode comprises any one or both of the compound represented by the formula (2a-2) and the compound represented by the formula (2b-2).

In one embodiment, the compound represented by the formula (1) contained in the emitting layer is a compound represented by the above formula (1-3), and the compound represented by the formula (2) contained in at least one layer between the emitting layer and the anode comprises any one or both of the compound represented by the formula (2a-3) and the compound represented by the formula (2b-3).

In one embodiment, the compound represented by the formula (1) contained in the emitting layer is a compound represented by the above formula (1-4), and the compound represented by the formula (2) contained in at least one layer between the emitting layer and the anode is the compound represented by the formula (2a-4).

In one embodiment, the organic layer between the emitting layer and the anode includes the hole-injecting layer and the hole-transporting layer, and the hole-transporting layer contains the compound represented by the formula (2).

In one embodiment, the hole-transporting layer that is adjacent to the emitting layer contains the compound represented by the formula (2).

The device configuration of the organic EL device according to one embodiment of the invention includes at least anode/(at least one organic layer between the emitting layer and the anode)/emitting layer/cathode, and the emitting layer comprises the compound (1) and at least one organic layer between the emitting layer and the anode comprises the compound (2).

As long as the device has the emitting layer comprising the compound (1) and at least one organic layer between the emitting layer and the anode that comprises the compound (2), other organic layers may be provided between the emitting layer and the anode, and one or more organic layers may be provided between the emitting layer and the cathode.

FIG. 1 shows a schematic configuration of one example of the organic EL device according to one embodiment of the invention.

An organic EL device 1 comprises a substrate 2, an anode 3, a cathode 4 and an organic layer 10 arranged between the anode 3 and the cathode 4.

The organic layer 10 has the above-mentioned emitting layer 5, and has the hole-injecting and/or transporting layer 6 is provided between the emitting layer 5 and the anode 3. An electron-injecting and/or transporting layer 7 or the like may be provided between the emitting layer 5 and the cathode 4.

Here, the "hole-injecting and/or transporting layer" means "at least one of the hole-injecting layer and the hole-transporting layer", and the "electron-injecting and/or transporting layer" means "at least one of the electron-injecting layer and the electron-transporting layer".

An electron barrier layer may be provided on the anode 3 side of the emitting layer 5 and a hole barrier layer may be provided on the cathode 4 side of the emitting layer 5.

Due to such configuration, electrons or holes are confined in the emitting layer 5, the possibility of formation of excitons in the emitting layer 5 can be increased.

In addition to each layer mentioned above, an organic semiconductor layer, an adhesion improvement layer, an insulation layer or the like may be provided between the emitting layer and the anode or between the emitting layer and the cathode.

In one embodiment, it is preferred that the compound (1) be a host material of the emitting layer.

The emitting layer that comprises the compound (1) may be either a phosphorescent emitting layer or a fluorescent emitting layer, or may be plural layers. It is preferred that the emitting layer that comprises the compound (1) be a fluorescent emitting layer. When plural emitting layers are present, a space layer may be provided between the emitting layers in order to prevent excitons formed in the phosphorous emitting layer from scattering to the fluorescent emitting layer.

Further, the emitting layer that comprises the compound (1) may comprise any one or both of the fluorescent dopant and the phosphorescent dopant. It is preferred that the emitting layer that comprises the compound (1) contain a fluorescent dopant.

As the fluorescent dopant and the phosphorescent dopant, a fluorescent emitting material and a phosphorescent emitting material as a guest material of the emitting layer, mentioned later, etc. can be given.

In the organic EL device according to one aspect of the invention, known materials and device configurations may be applied as long as the emitting layer comprises the compound (1) and the at least one layer between the emitting layer and the anode comprises the compound (2).

Hereinbelow, an explanation will be made on elements and materials other than the compounds (1) and (2) constituting each layer that can be used in the organic EL device according to one embodiment of the invention.

(Substrate)

The substrate is used as a supporting body of the emitting device. As the substrate, glass, quarts, plastic or the like can be used. Further, a flexible substrate may be used. The flexible substrate means a substrate that can be bent. For example, a plastic substrate made of polycarbonate or vinyl polychloride or the like can be given.

(Anode)

In an anode formed on a substrate, it is preferable to use a metal having a large work function (specifically, 4.0 eV or more), an alloy, an electric conductive compound, a mixture of these or the like. Specifically, indium oxide-tin oxide (ITO: Indium Tin Oxide), indium oxide-tin oxide containing silicon or silicon oxide, indium oxide-zinc oxide, tungsten oxide, indium oxide containing zinc oxide, graphene, or the like can be given. In addition, gold (Au), platinum (Pt) or a nitride of a metal material (titanium nitride) or the like can be given.

(Hole-Injecting Layer)

The hole-injecting layer is a layer containing a substance having a high hole-injecting property. As a substance having a high hole-injecting property, a substance selected from molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, a polymer compound (oligomer, dendrimer, polymer, etc.) or the like can also be used (Hole-Transporting Layer)

The hole-transporting layer is a layer containing a substance having a high hole-transporting property. For the hole-transporting layer, aromatic amine compounds, carbazole derivatives, anthracene derivatives and the like can be used. Polymer compounds such as poly (N-vinylcarbazole) (abbreviation: PVK) and poly(4-vinyltriphenylamine) (abbreviation: PVTPA) can also be used. However, any substance other than these may be used as long as it is a substance having a higher transporting property for holes than electrons. Note that the layer containing a substance having a high hole-transporting property is not limited to a single layer, but may be a stacked body of two or more layers made of the above substances.

(Guest Material of the Emitting Layer)

The emitting layer is a layer that comprises a substance having high luminous property, and various materials can be used. For example, as the substance having high luminous property, a fluorescent compound that emits fluorescent light or a phosphorescent compound that emits phosphorescent light can be used. The fluorescent compound is a compound capable of emitting light from a singlet excited state and the phosphorescent compound is a compound capable of emitting light from a triplet excited state.

As a blue fluorescent material that can be used for the emitting layer, pyrene derivatives, styrylamine derivatives, chrysene derivatives, fluoranthene derivatives, fluorene derivatives, diamine derivatives, triarylamine derivatives and the like can be used. An aromatic amine derivative or the like can be used as a green fluorescent light-emitting material that can be used in the emitting layer. As a red fluorescent material which can be used in emitting layer, a tetracene derivative, a diamine derivative or the like can be used.

Metal complexes such as iridium complexes, osmium complexes, platinum complexes and the like are used as the blue phosphorescent material that can be used in the emitting layer. An iridium complex or the like is used as a green phosphorescent material that can be used in the emitting layer. Metal complexes such as iridium complexes, platinum complexes, terbium complexes, europium complexes and the like are used as red phosphorescent materials that can be used in the emitting layer.

(Host Material of Emitting Layer)

The emitting layer may have a structure in which the substance having high luminescent property (guest material) described above is dispersed in another substance (host material). Various materials can be used as substances for dispersing substances with high luminescent properties, and it is preferable to use a material having a high lowest unoccupied molecular orbital level (LUMO level) and a low highest occupied molecular orbital level (HOMO level), rather than a material having a high luminous property.

As a substance (host material) for dispersing a substance having a high luminous property, 1) a metal complex such as an aluminum complex, a beryllium complex or a zinc complex, 2) a heterocyclic compound such as an oxadiazole derivative, a benzimidazole derivative, a phenanthroline derivative or the like, 3) a fused aromatic compound such as a carbazole derivative, an anthracene derivative, a phenanthrene derivative, a pyrene derivative or a chrysene derivative, and 4) an aromatic amine compound such as a triarylamine derivative or a fused polycyclic aromatic amine derivative are used.

(Electron-Transporting Layer)

The electron-transporting layer is a layer containing a substance having a high electron-transporting property. For the electron-transporting layer, 1) a metal complex such as an aluminum complex, a beryllium complex, or a zinc complex, 2) a heteroaromatic compound such as an imidazole derivative, a benzimidazole derivative, an azine derivative, a carbazole derivative or a phenanthroline derivative, and 3) a polymer compound can be used.

(Electron-Injecting Layer)

The electron-injection layer is a layer containing a substance having a high electron-injection property. For the electron-injection layer, alkali metals, alkaline earth metals or a compound thereof such as lithium (Li), lithium fluoride (LiF), cesium fluoride (CsF), calcium fluoride ($CaF_2$), lithium oxide ($LiO_x$) or the like can be used.

(Cathode)

It is preferable to use a metal, an alloy, an electrically conductive compound, a mixture thereof, or the like having a small work function (specifically, 3.8 eV or less) for the cathode. Specific examples of such cathode material include elements belonging to Group 1 or Group 2 of the periodic table of elements, that is, alkali metals such as lithium (Li) and cesium (Cs), alkaline earth metals such as magnesium (Mg).

In the organic EL device according to one aspect of the invention, the method for forming each layer is not particularly restricted. A conventionally known forming method such as a vacuum deposition method, a spin coating method or the like can be used. Each layer such as the emitting layer or the like can be formed by a vacuum deposition method, a molecular beam evaporation method (MBE method), or a known coating method such as a dipping method, a solution spin coating method, a casting method, a bar coating method, or the like, that uses a solution of a material forming each layer dissolved in a solvent.

In the organic EL device according to one aspect of the invention, the thickness of each layer is not particularly restricted. In general, in order to suppress occurrence of defects such as pinholes and to suppress the applied voltage and to improve luminous efficiency, the thickness is normally preferably in a range of several nm to 1 µm.

The organic EL device according to one aspect of the invention can be used as an electronic device including a display element such as an organic EL panel module; a display such as a TV, a mobile phone or a PC; and emitting devices such as lightings and lights for automobiles or the like.

EXAMPLES

The invention will be explained in more detail with the Examples and the Comparative Examples, which should not be construed as limiting the scope of the invention.

Example 1

(Fabrication of Organic EL Device)

A glass substrate of 25 mm by 75 mm by 1.1 mm thick with an ITO transparent electrode (anode) was subjected to ultrasonic cleaning with isopropyl alcohol for 5 minutes, and then subjected to UV-ozone cleaning for 30 minutes. The thickness of the ITO was 130 nm.

The cleaned glass substrate with a transparent electrode was mounted in a substrate holder of a vacuum vapor deposition apparatus. First, the compound HIL was deposited on the surface where the transparent electrode was formed so as to cover the transparent electrode, thereby to form a 5 nm-thick HIL film was formed. This HIL film serves as a hole-injecting layer.

Subsequent to the formation of the HIL film, the compound HTL was deposited, whereby a 90 nm-thick HTL film was formed on the HIL film. This HTL film serves as a first hole-transporting layer.

Subsequent to the formation of the HTL film, the compound HT-1 was deposited, whereby a 5 nm-thick HT-1 film was formed on the HTL film. This HT-1 film serves as a second hole-transporting layer.

On the HT-1 film, BH-1 (host material) and BD (dopant material) were co-deposited such that the amount ratio of BD (mass ratio) became 4%, whereby a 20 nm-thick emitting layer was formed.

On this emitting layer, HBL was deposited to form a 5 nm-thick electron-transporting layer. On this electron-transporting layer, ETL and Liq as the electron-injecting materials were co-deposited such that the amount ratio (mass ratio) of Liq become 50%, whereby a 20 nm-thick electron-injecting layer was formed. On this electron-injecting layer, Liq was deposited, whereby a 1 nm-thick Liq film was formed. On this Liq film, metal Al was deposited, whereby a 80 nm-thick metal cathode was formed.

By the above-mentioned procedures, an organic EL device was fabricated. The compounds used in Example 1 are shown below.

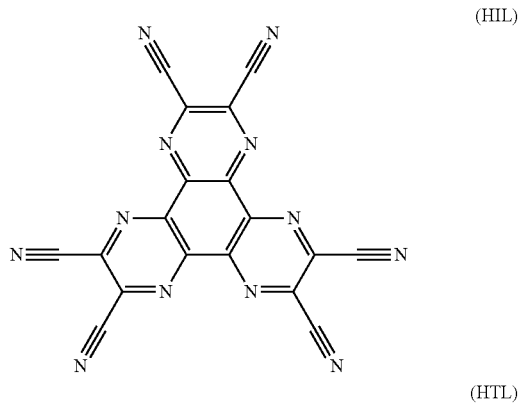

(HIL)

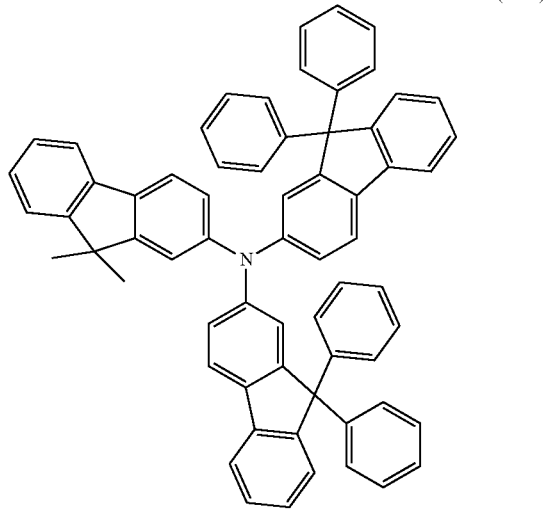

(HTL)

-continued

HT-1
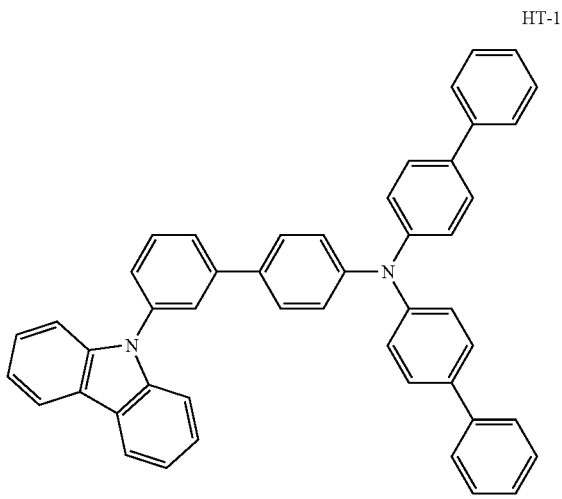

BH-1
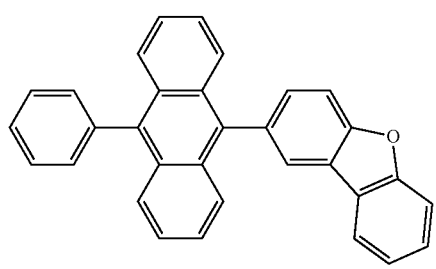

(BD)
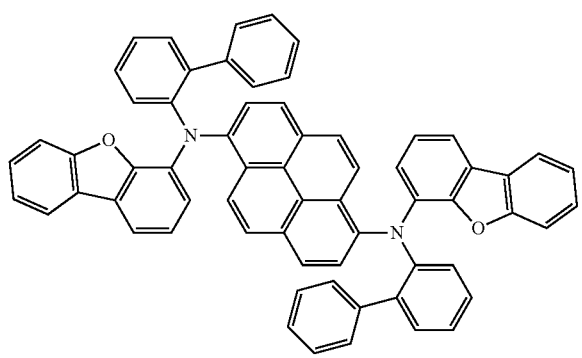

(HBL)
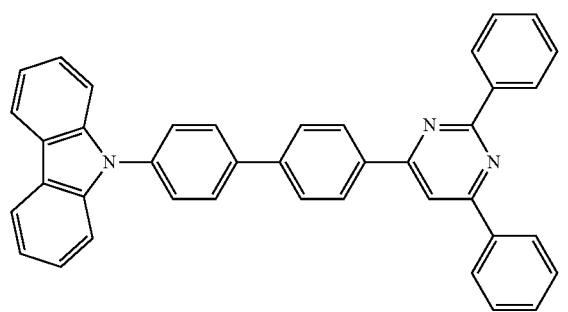

-continued (ETL)
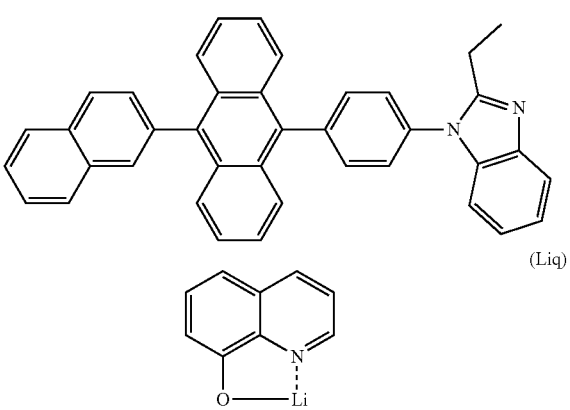

(Liq)

(Evaluation of Organic EL Device)

A voltage was applied to the resulting organic EL device such that the current density became 10 mA/cm$^2$, and an EL emission spectrum was measured by means of a spectroradiometer (CS-1000 manufactured by Konica Minolta, Inc.). From the resulting spectral radiance spectrum, an external quantum efficiency EQE (%) was calculated. The results are shown in Table 1.

Further, a voltage was applied to the organic EL device such that the current density became 50 mA/cm$^2$, and the time taken until the luminance became 90% of the initial luminance (lifetime, LT90) were measured, and the results are shown in Table 1.

Examples 2 to 11 and Comparative
Examples 1 to 2

Organic EL devices were fabricated and evaluated in the same manner as in Example 1, except that the compounds shown in Table 1 were used as the second hole-transporting material and the host material of the emitting layer. The results are shown in Table 1.

Compounds used in Examples 1 to 11 and Comparative Examples 1 to 2 are shown below.

HT-1
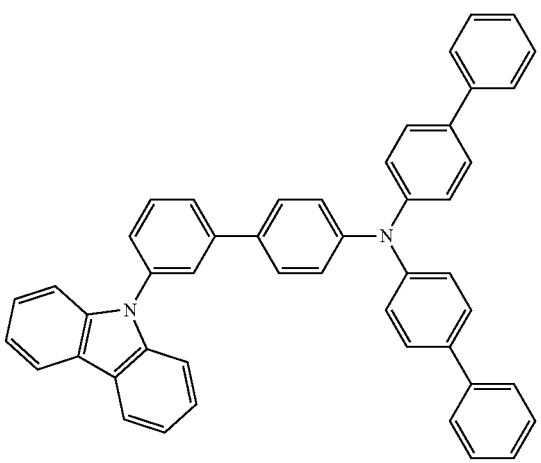

HT-2
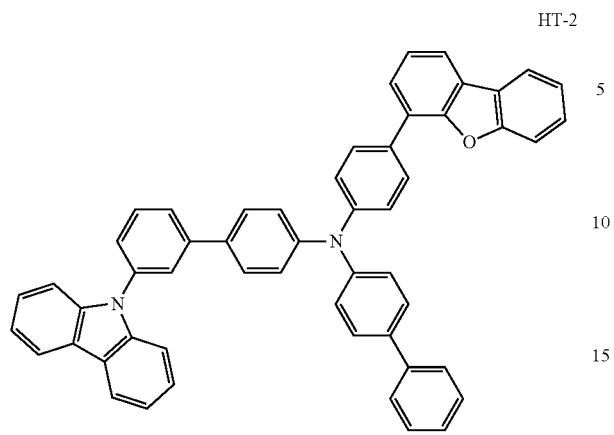
BH-5
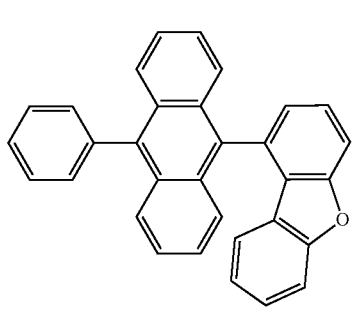
BH-1
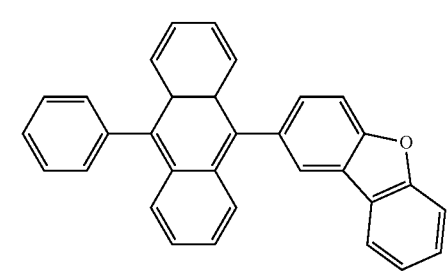
BH-6
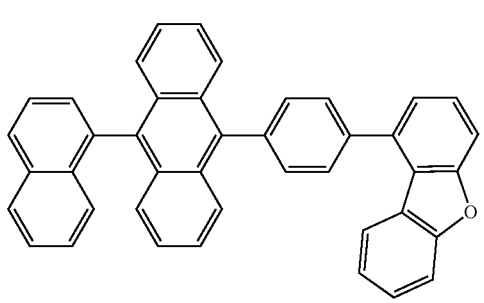
BH-2
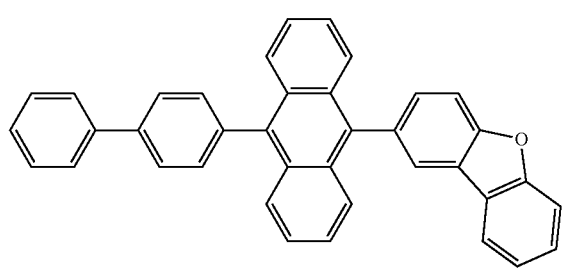
BH-7
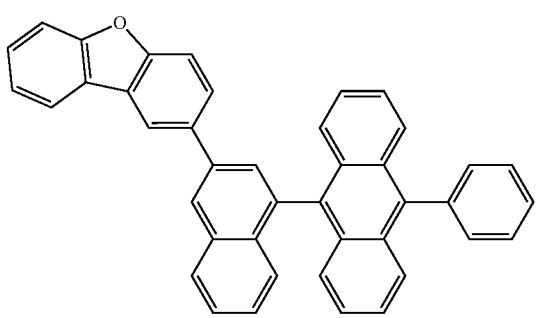
BH-3
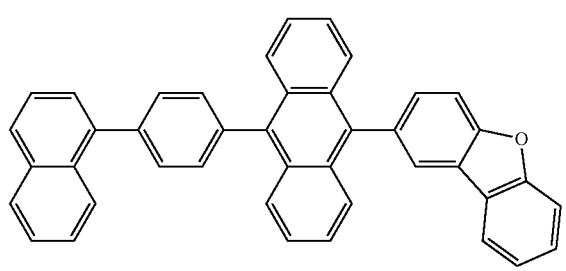
BH-8
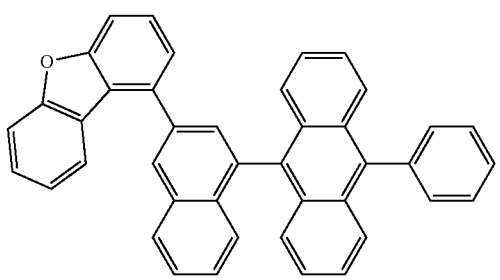
BH-4
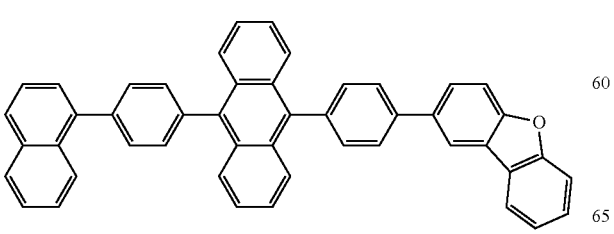
BH-A
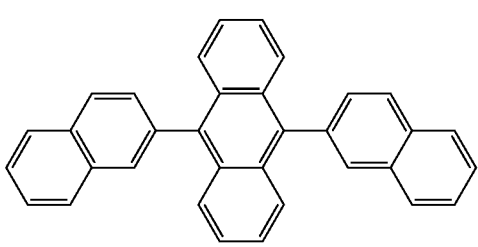

-continued

BH-B

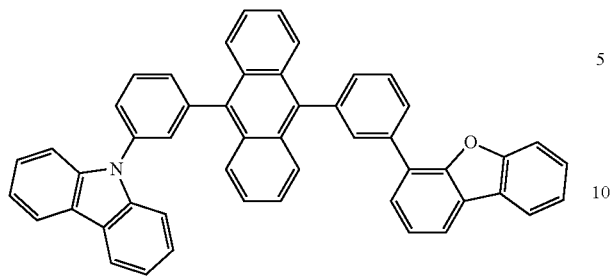

TABLE 1

| | Material for second hole-transporting layer | Host material for emitting layer | External quantum efficiency EQE (%) | Lifetime LT90 (hr) |
|---|---|---|---|---|
| Example 1 | HT-1 | BH-1 | 9.8 | 140 |
| Example 2 | HT-2 | BH-1 | 9.9 | 155 |
| Example 3 | HT-1 | BH-2 | 10.0 | 150 |
| Example 4 | HT-2 | BH-2 | 9.8 | 160 |
| Example 5 | HT-1 | BH-3 | 10.1 | 140 |
| Example 6 | HT-1 | BH-4 | 9.8 | 145 |
| Example 7 | HT-1 | BH-5 | 10.0 | 140 |
| Example 8 | HT-2 | BH-5 | 9.9 | 150 |
| Example 9 | HT-1 | BH-6 | 9.8 | 155 |
| Example 10 | HT-1 | BH-7 | 9.8 | 135 |
| Example 11 | HT-1 | BH-8 | 9.9 | 140 |
| Comp. Ex. 1 | HT-1 | BH-A | 9.2 | 95 |
| Comp. Ex. 2 | HT-1 | BH-B | 8.9 | 50 |

From the results indicated in Table 1, the organic EL devices in Examples 1 to 6 in which BH-1 to BH-6 were used as the host materials of the emitting layer and HT-1 or HT-2 was used in the hole-transporting layer (second hole-transporting layer) that is adjacent to the emitting layer had a higher external quantum efficiency as compared with the organic EL devices in Comparative Examples 1 and 2 in which BH-A or BH-B was used in the hole-transporting layer that is adjacent to the emitting layer.

In addition, the organic EL devices of Examples 1 to 11 had a longer device life (LT90) as compared with the organic EL devices of Comparative Examples 1 to 2.

From the above, it was confirmed that the organic EL device according to one embodiment of the invention in which the compound (1) was used in the emitting layer and the compound (2) was used in the hole-transporting layer that is adjacent to the emitting layer had excellent luminous efficiency.

EXPLANATION OF NUMERICAL SYMBOLS

1. Organic EL device
2. Substrate
3. Anode
4. Cathode
5. Emitting layer
6. Hole-injecting and/or transporting layer
7. Electron-injecting and/or transporting layer
10. Organic layer

The invention claimed is:

1. An organic electroluminescence device comprising an anode, a cathode and an organic layer between the anode and the cathode, the organic layer comprising an emitting layer and at least one layer between the emitting layer and the anode, the emitting layer comprising a compound represented by the following formula (1), and the at least one layer between the emitting layer and the anode comprising a compound represented by the following formula (2a):

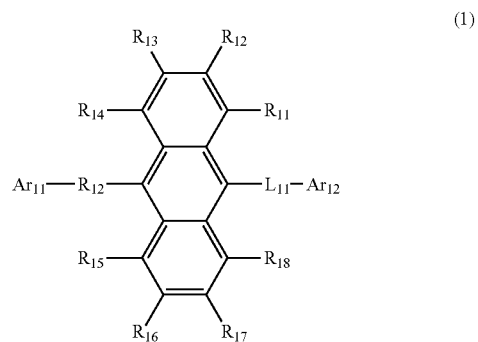

wherein in the formula (1),
$R_{11}$ to $R_{18}$ are hydrogen atoms,
$Ar_{12}$ is a monovalent group represented by the following formula (11):

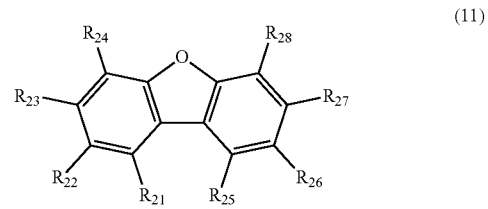

wherein in the formula (11),
one of $R_{21}$ to $R_{28}$ is a single bond bonding to $L_{11}$,
$R_{21}$ to $R_{28}$ that do not bond to $L_{11}$ are independently a hydrogen atom, or an unsubstituted phenyl group,
$Ar_{11}$ is an unsubstituted phenyl group,
$L_{12}$ is a single bond, or an unsubstituted phenylene group, and
$L_{11}$ is an unsubstituted naphthylene group, and

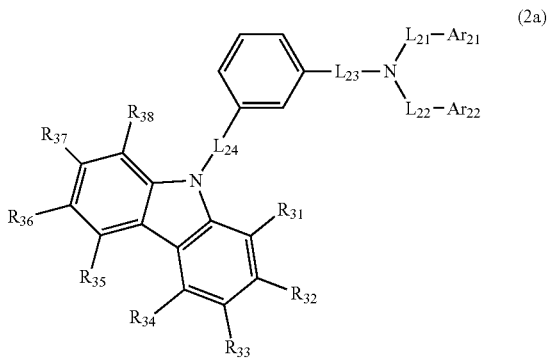

wherein in the formula (2a),
$R_{31}$ to $R_{38}$ are hydrogen atoms,
$L_{21}$ and $L_{22}$ are independently a single bond, or an unsubstituted phenylene group, $L_{23}$ is an unsubstituted phenylene group,
$L_{24}$ is a single bond, and
$Ar_{21}$ and $Ar_{22}$ are independently an unsubstituted phenyl group, or an unsubstituted biphenylyl group.

2. The organic electroluminescence device according to claim 1, wherein the compound represented by the formula (1) is a compound represented by the following formula (1-1):

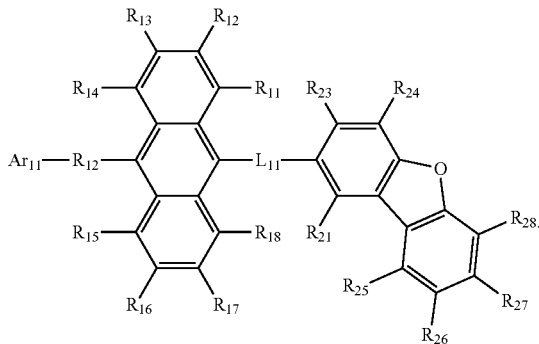

(1-1)

wherein in the formula (1-1), $R_{11}$ to $R_{18}$, $Ar_{11}$, $L_{11}$, $L_{12}$, $R_{21}$ and $R_{23}$ to $R_{28}$ are as defined in the formula (1).

3. The organic electroluminescence device according to claim 1, wherein $R_{21}$ to $R_{28}$ that do not bond to $L_{11}$ are hydrogen atoms.

4. The organic electroluminescence device according to claim 1, wherein the organic layer between the emitting layer and the anode comprises a hole-injecting layer and a hole-transporting layer, and the hole-transporting layer comprises the compound represented by the formula (2a).

5. The organic electroluminescence device according to claim 4, wherein the hole-transporting layer is adjacent to the emitting layer.

6. The organic electroluminescence device according to claim 1, wherein the emitting layer further comprises any one or both of a fluorescent dopant and a phosphorescent dopant.

7. An electronic device provided with the organic electroluminescence device according to claim 1.

8. The organic electroluminescence device according to claim 1, wherein the compound represented by the formula (1) is a compound represented by the following formula (1-1H):

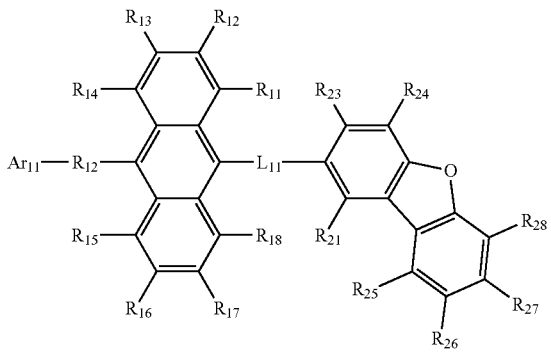

(1-1H)

wherein in the formula (1-1H), $R_{23}$ to $R_{28}$ are hydrogen atoms, and $R_{11}$ to $R_{18}$, $Ar_{11}$, $L_{11}$, $L_{12}$ and $R_{21}$ are as defined in the formula (1).

9. The organic electroluminescence device according to claim 1, wherein $L_{12}$ is a single bond.

10. The organic electroluminescence device according to claim 8, wherein $L_{11}$ is an unsubstituted 1,2-naphthylene group, an unsubstituted 1,3-naphthylene group or an unsubstituted 1,4-naphthylene group.

11. The organic electroluminescence device according to claim 1, wherein both of $L_{21}$ and $L_{22}$ are single bonds.

12. The organic electroluminescence device according to claim 1, wherein both of $Ar_{21}$ and $Ar_{22}$ are unsubstituted biphenylyl group.

13. The organic electroluminescence device according to claim 1, wherein $L_{21}$ is a single bond, and $Ar_{21}$ is an unsubstituted biphenylyl group.

14. The organic electroluminescence device according to claim 1, wherein $L_{23}$ is an unsubstituted p-phenylene group.

15. The organic electroluminescence device according to claim 2, wherein $L_{23}$ is an unsubstituted p-phenylene group.

16. The organic electroluminescence device according to claim 8, wherein $L_{23}$ is an unsubstituted p-phenylene group.

17. The organic electroluminescence device according to claim 1, wherein both of $L_{21}$ and $L_{22}$ are single bonds, and both of $Ar_{21}$ and $Ar_{22}$ are unsubstituted biphenylyl groups.

18. The organic electroluminescence device according to claim 2, wherein both of $L_{21}$ and $L_{22}$ are single bonds, and both of $Ar_{21}$ and $Ar_{22}$ are unsubstituted biphenylyl groups.

19. The organic electroluminescence device according to claim 8, wherein both of $L_{21}$ and $L_{22}$ are single bonds, and both of $Ar_{21}$ and $Ar_{22}$ are unsubstituted biphenylyl groups.

20. The organic electroluminescence device according to claim 1, wherein $L_{21}$ is a single bond, and $Ar_{21}$ is an unsubstituted 4-biphenylyl group.

21. The organic electroluminescence device according to claim 2, wherein $L_{21}$ is a single bond, and $Ar_{21}$ is an unsubstituted 4-biphenylyl group.

22. The organic electroluminescence device according to claim 8, wherein $L_{21}$ is a single bond, and $Ar_{21}$ is an unsubstituted 4-biphenylyl group.

23. The organic electroluminescence device according to claim 1, wherein both of $L_{21}$ and $L_{22}$ are single bonds, and both of $Ar_{21}$ and $Ar_{22}$ are unsubstituted 4-biphenylyl groups.

24. The organic electroluminescence device according to claim 2, wherein both of $L_{21}$ and $L_{22}$ are single bonds, and both of $Ar_{21}$ and $Ar_{22}$ are unsubstituted 4-biphenylyl groups.

25. The organic electroluminescence device according to claim 1, wherein both of $L_{21}$ and $L_{22}$ are single bonds, both of $Ar_{21}$ and $Ar_{22}$ are unsubstituted 4-biphenylyl groups, and $L_{23}$ is an unsubstituted p-phenylene group.

26. The organic electroluminescence device according to claim 2, wherein both of $L_{21}$ and $L_{22}$ are single bonds, both of $Ar_{21}$ and $Ar_{22}$ are unsubstituted 4-biphenylyl groups, and $L_{23}$ is an unsubstituted p-phenylene group.

* * * * *